US006855801B1

(12) United States Patent
San Antonio et al.

(10) Patent No.: US 6,855,801 B1
(45) Date of Patent: Feb. 15, 2005

(54) PEPTIDES MODULATING ACTIVITIES OF HEPARIN OTHER GLYCOSAMINOGLYCANS OR PROTEOGLYCANS

(75) Inventors: James D. San Antonio, Media, PA (US); Angela Verrecchio, Brighton, MA (US); Barbara P. Schick, Merion Station, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/496,391

(22) Filed: Feb. 2, 2000

Related U.S. Application Data

(60) Provisional application No. 60/118,276, filed on Feb. 2, 1999.

(51) Int. Cl.[7] .............................. C07K 4/00; C07K 7/06; C07K 9/00
(52) U.S. Cl. ........................ 530/300; 530/328; 530/329
(58) Field of Search ................................. 530/300, 328, 530/329

(56) References Cited

FOREIGN PATENT DOCUMENTS

WO     WO 93/13119    *  1/1990

OTHER PUBLICATIONS

Accession No. AAR42842, Nov. 24, 1993.*
Accession No. AAR05247, Aug. 4, 1990.*
deBoar et al (The Journal of Biological Chemistry, 1992, vol. 267, pp. 2264–2268).*
Wakefield et al (Surgical Research, 1994, vol. 56, pp. 586–593).*
Mathews and Van Holde, Biochemistry, 1996, pp. 165–171.*
Matthews, B. "Genetic and Structural Analysis of the Protein Stability Problem", In: Perspectives in Biochemistry, Neurath, Ed. 1989, American Chemical Society.*
Verrechio A et al. (2000), "Design of peptides with high afinities for heparin and endothelial cell proteoglycans," *J. Biol. Chem.* 275: 7701–7707.
Cardin AD, Weintraub HJ (1989), "Molecular modeling of protein–glycosaminoglycan interactions," *Arterioscler.* 9: 21–32.
Margalit H et al. (1993), "Comparative Analysis of Structurally Defined Heparin Binding Sequences Reveals a Distinct Spatial distribution of Basic Residues," *J. Biol. Chem.* 268: 19228–19231.
Fromm JR et al. (1997), "Pattern and Spacing of Basic Amino Acids in Heparin Binding Sites," *Archives of Biochemistry and Biophysics* 343: 92–100.
Hileman RE et al. (1998), "Glycosaminoglycan–protein Interactions; Definition of Consensus Sites in Glycosaminoglycan Binding Proteins," *BioEssays* 20:156–157.

* cited by examiner

*Primary Examiner*—Karen A. Canella
(74) *Attorney, Agent, or Firm*—Drinker Biddle & Reath LLP

(57) ABSTRACT

The present invention involves peptides of various sequences and sizes and methods of using said peptides with a strong affinity for glycosaminoglycans and proteoglycans, wherein said peptides interact strongly with heparin, other glycosaminoglycans, or proteoglycans (PGs).

13 Claims, 11 Drawing Sheets

(ARKKAAKA)$_4$ EC PGs (ARKKAAKA)$_4$ EC PGs/NA (ARRRAARA)$_3$

[PEPTIDE], nM

Figure 1:
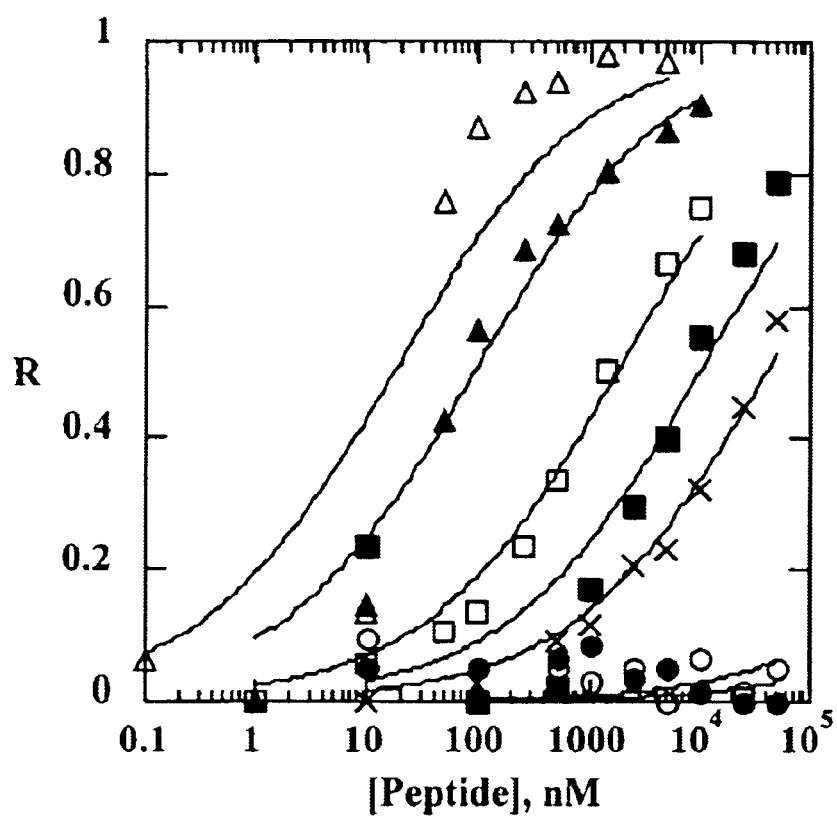

SEQUENCE LISTING

<160> NUMBER OF SEQ ID NOS: 58

<210> SEQ ID NO 1
<211> LENGTH: 6
<212> TYPE: PRT
<213> ORGANISM: Artificial Sequence
<220> FEATURE:
<223> OTHER INFORMATION: protein fragment -continued

```
<400> SEQUENCE: 1

Gly Arg Arg Leu Lys Asp
1               5

<210> SEQ ID NO 2
<211> LENGTH: 11
<212> TYPE: PRT
<213> ORGANISM: Artificial Sequence
<220> FEATURE:
<223> OTHER INFORMATION: protein fragment

<400> SEQUENCE: 2

Ser Leu Arg Met Asn Gly Cys Gly Ala His Gln
1               5                  10

<210> SEQ ID NO 3
<211> LENGTH: 7
<212> TYPE: PRT
<213> ORGANISM: Artificial Sequence
<220> FEATURE:
<223> OTHER INFORMATION: protein fragment

<400> SEQUENCE: 3

Tyr Tyr His Tyr Lys Val Asn
1               5

<210> SEQ ID NO 4
<211> LENGTH: 6
<212> TYPE: PRT
<213> ORGANISM: Artificial Sequence
<220> FEATURE:
<223> OTHER INFORMATION: protein fragment

<400> SEQUENCE: 4

Ala Lys Lys Ala Arg Ala
1               5

<210> SEQ ID NO 5
<211> LENGTH: 8
<212> TYPE: PRT
<213> ORGANISM: Artificial Sequence
<220> FEATURE:
<223> OTHER INFORMATION: protein fragment

<400> SEQUENCE: 5

Ala Arg Lys Lys Ala Ala Lys Ala
1               5

<210> SEQ ID NO 6
<211> LENGTH: 16
<212> TYPE: PRT
<213> ORGANISM: Artificial Sequence
<220> FEATURE:
<223> OTHER INFORMATION: protein fragment

<400> SEQUENCE: 6

Ala Arg Lys Lys Ala Ala Lys Ala Ala Arg Lys Lys Ala Ala Lys Ala
1               5                  10                  15

<210> SEQ ID NO 7
<211> LENGTH: 18
<212> TYPE: PRT
<213> ORGANISM: Artificial Sequence
<220> FEATURE:
<223> OTHER INFORMATION: protein fragment
```

```
<400> SEQUENCE: 7

Ala Lys Lys Ala Arg Ala Ala Lys Lys Ala Arg Ala Ala Lys Lys Ala
 1               5                   10                  15

Arg Ala

<210> SEQ ID NO 8
<211> LENGTH: 32
<212> TYPE: PRT
<213> ORGANISM: Artificial Sequence
<220> FEATURE:
<223> OTHER INFORMATION: protein fragment

<400> SEQUENCE: 8

Ala Arg Lys Lys Ala Ala Lys Ala Ala Arg Lys Lys Ala Ala Lys Ala
 1               5                   10                  15

Ala Arg Lys Lys Ala Ala Lys Ala Ala Arg Lys Lys Ala Ala Lys Ala
                20                  25                  30

<210> SEQ ID NO 9
<211> LENGTH: 15
<212> TYPE: PRT
<213> ORGANISM: Artificial Sequence
<220> FEATURE:
<223> OTHER INFORMATION: protein fragment

<400> SEQUENCE: 9

Tyr Pro Ala Arg Arg Ala Arg Tyr Gln Trp Val Arg Cys Lys Pro
 1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: protein fragment

<400> SEQUENCE: 10

Tyr Pro Thr Gln Arg Ala Arg Tyr Gln Trp Val Arg Cys Asn Pro
 1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: protein fragment

<400> SEQUENCE: 11

Ala Ala Ala Arg Arg Ala Arg Ala Ala Ala Ala Arg Ala Lys Ala
 1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: protein fragment

<400> SEQUENCE: 12

Tyr Pro Ala Arg Arg Ala Arg Tyr Gln Trp Val Arg Ala Lys Pro
 1               5                   10                  15
```

```
<210> SEQ ID NO 13
<211> LENGTH: 36
<212> TYPE: PRT
<213> ORGANISM: Artificial Sequence
<220> FEATURE:
<223> OTHER INFORMATION: protein fragment

<400> SEQUENCE: 13

Ala Lys Lys Ala Arg Ala Ala Lys Lys Ala Arg Ala Ala Lys Lys Ala
 1               5                  10                  15

Arg Ala Ala Lys Lys Ala Arg Ala Ala Lys Lys Ala Arg Ala Ala Lys
                20                  25                  30

Lys Ala Arg Ala
        35

<210> SEQ ID NO 14
<211> LENGTH: 12
<212> TYPE: PRT
<213> ORGANISM: Artificial Sequence
<220> FEATURE:
<223> OTHER INFORMATION: protein fragment

<400> SEQUENCE: 14

Ala Lys Lys Ala Arg Ala Ala Lys Lys Ala Arg Ala
 1               5                  10

<210> SEQ ID NO 15
<211> LENGTH: 8
<212> TYPE: PRT
<213> ORGANISM: Artificial Sequence
<220> FEATURE:
<223> OTHER INFORMATION: protein fragment

<400> SEQUENCE: 15

Ala Lys Ala Ala Lys Lys Arg Ala
 1               5

<210> SEQ ID NO 16
<211> LENGTH: 6
<212> TYPE: PRT
<213> ORGANISM: Artificial Sequence
<220> FEATURE:
<223> OTHER INFORMATION: protein fragment

<400> SEQUENCE: 16

Ala Arg Ala Lys Lys Ala
 1               5

<210> SEQ ID NO 17
<211> LENGTH: 8
<212> TYPE: PRT
<213> ORGANISM: Artificial Sequence
<220> FEATURE:
<223> OTHER INFORMATION: protein fragment

<400> SEQUENCE: 17

Ala Arg Arg Arg Ala Ala Arg Ala
 1               5

<210> SEQ ID NO 18
<211> LENGTH: 8
<212> TYPE: PRT
<213> ORGANISM: Artificial Sequence
<220> FEATURE:
<223> OTHER INFORMATION: protein fragment
```

```
<400> SEQUENCE: 18

Ala Arg Arg Lys Ala Ala Lys Ala
 1               5

<210> SEQ ID NO 19
<211> LENGTH: 8
<212> TYPE: PRT
<213> ORGANISM: Artificial Sequence
<220> FEATURE:
<223> OTHER INFORMATION: protein fragment

<400> SEQUENCE: 19

Ala Lys Lys Arg Ala Ala Lys Ala
 1               5

<210> SEQ ID NO 20
<211> LENGTH: 8
<212> TYPE: PRT
<213> ORGANISM: Artificial Sequence
<220> FEATURE:
<223> OTHER INFORMATION: protein fragment

<400> SEQUENCE: 20

Ala Arg Ala Ala Arg Arg Arg Ala
 1               5

<210> SEQ ID NO 21
<211> LENGTH: 8
<212> TYPE: PRT
<213> ORGANISM: Artificial Sequence
<220> FEATURE:
<223> OTHER INFORMATION: protein fragment

<400> SEQUENCE: 21

Ala Arg Ala Ala Lys Arg Lys Ala
 1               5

<210> SEQ ID NO 22
<211> LENGTH: 8
<212> TYPE: PRT
<213> ORGANISM: Artificial Sequence
<220> FEATURE:
<223> OTHER INFORMATION: protein fragment

<400> SEQUENCE: 22

Gly Arg Arg Lys Gly Gly Arg Gly
 1               5

<210> SEQ ID NO 23
<211> LENGTH: 8
<212> TYPE: PRT
<213> ORGANISM: Artificial Sequence
<220> FEATURE:
<223> OTHER INFORMATION: protein fragment

<400> SEQUENCE: 23

Gly Arg Lys Lys Gly Gly Arg Gly
 1               5

<210> SEQ ID NO 24
<211> LENGTH: 8
<212> TYPE: PRT
<213> ORGANISM: Artificial Sequence
<220> FEATURE:
<223> OTHER INFORMATION: protein fragment
```

```
<400> SEQUENCE: 24

Gly Lys Lys Lys Gly Gly Arg Gly
  1               5

<210> SEQ ID NO 25
<211> LENGTH: 8
<212> TYPE: PRT
<213> ORGANISM: Artificial Sequence
<220> FEATURE:
<223> OTHER INFORMATION: protein fragment

<400> SEQUENCE: 25

Gly Arg Gly Gly Lys Arg Arg Gly
  1               5

<210> SEQ ID NO 26
<211> LENGTH: 8
<212> TYPE: PRT
<213> ORGANISM: Artificial Sequence
<220> FEATURE:
<223> OTHER INFORMATION: protein fragment

<400> SEQUENCE: 26

Gly Arg Gly Gly Lys Lys Arg Gly
  1               5

<210> SEQ ID NO 27
<211> LENGTH: 6
<212> TYPE: PRT
<213> ORGANISM: Artificial Sequence
<220> FEATURE:
<223> OTHER INFORMATION: protein fragment

<400> SEQUENCE: 27

Ala Arg Arg Ala Arg Ala
  1               5

<210> SEQ ID NO 28
<211> LENGTH: 6
<212> TYPE: PRT
<213> ORGANISM: Artificial Sequence
<220> FEATURE:
<223> OTHER INFORMATION: protein fragment

<400> SEQUENCE: 28

Ala Arg Lys Ala Lys Ala
  1               5

<210> SEQ ID NO 29
<211> LENGTH: 6
<212> TYPE: PRT
<213> ORGANISM: Artificial Sequence
<220> FEATURE:
<223> OTHER INFORMATION: protein fragment

<400> SEQUENCE: 29

Ala Arg Ala Arg Arg Ala
  1               5

<210> SEQ ID NO 30
<211> LENGTH: 6
<212> TYPE: PRT
<213> ORGANISM: Artificial Sequence
<220> FEATURE:
<223> OTHER INFORMATION: protein fragment
```

```
<400> SEQUENCE: 30

Ala Arg Ala Lys Lys Ala
 1               5

<210> SEQ ID NO 31
<211> LENGTH: 6
<212> TYPE: PRT
<213> ORGANISM: Artificial Sequence
<220> FEATURE:
<223> OTHER INFORMATION: protein fragment

<400> SEQUENCE: 31

Gly Arg Arg Gly Lys Gly
 1               5

<210> SEQ ID NO 32
<211> LENGTH: 6
<212> TYPE: PRT
<213> ORGANISM: Artificial Sequence
<220> FEATURE:
<223> OTHER INFORMATION: protein fragment

<400> SEQUENCE: 32

Gly Lys Lys Gly Arg Gly
 1               5

<210> SEQ ID NO 33
<211> LENGTH: 6
<212> TYPE: PRT
<213> ORGANISM: Artificial Sequence
<220> FEATURE:
<223> OTHER INFORMATION: protein fragment

<400> SEQUENCE: 33

Gly Arg Gly Arg Lys Gly
 1               5

<210> SEQ ID NO 34
<211> LENGTH: 6
<212> TYPE: PRT
<213> ORGANISM: Artificial Sequence
<220> FEATURE:
<223> OTHER INFORMATION: protein fragment

<400> SEQUENCE: 34

Gly Lys Gly Lys Arg Gly
 1               5

<210> SEQ ID NO 35
<211> LENGTH: 16
<212> TYPE: PRT
<213> ORGANISM: Artificial Sequence
<220> FEATURE:
<223> OTHER INFORMATION: protein fragment

<400> SEQUENCE: 35

Ala Arg Arg Lys Ala Ala Arg Ala Ala Arg Arg Lys Ala Cys Arg Ala
 1               5                  10                  15

<210> SEQ ID NO 36
<211> LENGTH: 24
<212> TYPE: PRT
<213> ORGANISM: Artificial Sequence
<220> FEATURE:
<223> OTHER INFORMATION: protein fragment
```

-continued

```
<400> SEQUENCE: 36

Ala Arg Cys Ala Lys Lys Arg Ala Ala Arg Ala Ala Lys Lys Arg Ala
1               5                   10                  15

Ala Arg Ala Ala Lys Lys Arg Ala
            20

<210> SEQ ID NO 37
<211> LENGTH: 18
<212> TYPE: PRT
<213> ORGANISM: Artificial Sequence
<220> FEATURE:
<223> OTHER INFORMATION: protein fragment

<400> SEQUENCE: 37

Ala Arg Arg Ala Lys Ala Ala Arg Arg Ala Lys Ala Ala Arg Arg Cys
1               5                   10                  15

Lys Ala

<210> SEQ ID NO 38
<211> LENGTH: 12
<212> TYPE: PRT
<213> ORGANISM: Artificial Sequence
<220> FEATURE:
<223> OTHER INFORMATION: protein fragment

<400> SEQUENCE: 38

Ala Lys Cys Lys Arg Ala Ala Lys Ala Lys Arg Ala
1               5                   10

<210> SEQ ID NO 39
<211> LENGTH: 23
<212> TYPE: PRT
<213> ORGANISM: Artificial Sequence
<220> FEATURE:
<223> OTHER INFORMATION: protein fragment

<400> SEQUENCE: 39

Ala Arg Lys Lys Ala Ala Arg Ala Ala Ala Ala Ala Ala Ala Ala Ala
1               5                   10                  15

Arg Lys Lys Ala Ala Arg Ala
            20

<210> SEQ ID NO 40
<211> LENGTH: 31
<212> TYPE: PRT
<213> ORGANISM: Artificial Sequence
<220> FEATURE:
<223> OTHER INFORMATION: protein fragment

<400> SEQUENCE: 40

Ala Arg Lys Lys Ala Ala Arg Ala Ala Ala Ala Ala Ala Ala Ala Ala
1               5                   10                  15

Ala Ala Ala Ala Ala Ala Ala Ala Arg Lys Lys Ala Ala Arg Ala
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: protein fragment
```

```
<400> SEQUENCE: 41

Ala Lys Lys Ala Arg Ala Ala Lys Lys Ala Arg Ala Ala Lys Lys Ala
1               5                   10                  15

Arg Ala Ala Lys Lys Ala Arg Ala Ala Lys Lys Ala Arg Ala
            20                  25                  30

<210> SEQ ID NO 42
<211> LENGTH: 40
<212> TYPE: PRT
<213> ORGANISM: Artificial Sequence
<220> FEATURE:
<223> OTHER INFORMATION: protein fragment

<400> SEQUENCE: 42

Ala Arg Lys Lys Ala Ala Lys Ala Ala Arg Lys Lys Ala Ala Lys Ala
1               5                   10                  15

Ala Arg Lys Lys Ala Ala Lys Ala Ala Arg Lys Lys Ala Ala Lys Ala
            20                  25                  30

Ala Arg Lys Lys Ala Ala Lys Ala
            35                  40

<210> SEQ ID NO 43
<211> LENGTH: 24
<212> TYPE: PRT
<213> ORGANISM: Artificial Sequence
<220> FEATURE:
<223> OTHER INFORMATION: protein fragment

<400> SEQUENCE: 43

Ala Arg Lys Lys Ala Ala Lys Ala Ala Arg Lys Lys Ala Ala Lys Ala
1               5                   10                  15

Ala Arg Lys Lys Ala Ala Lys Ala
            20

<210> SEQ ID NO 44
<211> LENGTH: 24
<212> TYPE: PRT
<213> ORGANISM: Artificial Sequence
<220> FEATURE:
<223> OTHER INFORMATION: protein fragment

<400> SEQUENCE: 44

Gly Arg Lys Lys Gly Gly Lys Gly Gly Arg Lys Lys Gly Gly Lys Gly
1               5                   10                  15

Gly Arg Lys Lys Gly Gly Lys Gly
            20

<210> SEQ ID NO 45
<211> LENGTH: 24
<212> TYPE: PRT
<213> ORGANISM: Artificial Sequence
<220> FEATURE:
<223> OTHER INFORMATION: protein fragment

<400> SEQUENCE: 45

Leu Arg Lys Lys Leu Gly Lys Arg Leu Arg Lys Lys Leu Gly Lys Arg
1               5                   10                  15

Leu Arg Lys Lys Leu Gly Lys Arg
            20
```

```
<210> SEQ ID NO 46
<211> LENGTH: 24
<212> TYPE: PRT
<213> ORGANISM: Artificial Sequence
<220> FEATURE:
<223> OTHER INFORMATION: protein fragment

<400> SEQUENCE: 46

Thr Arg Lys Lys Leu Gly Lys Ile Thr Arg Lys Lys Leu Gly Lys Ile
 1               5                  10                  15

Thr Arg Lys Lys Leu Gly Lys Ile
            20

<210> SEQ ID NO 47
<211> LENGTH: 32
<212> TYPE: PRT
<213> ORGANISM: Artificial Sequence
<220> FEATURE:
<223> OTHER INFORMATION: protein fragment

<400> SEQUENCE: 47

Ala Arg Lys Lys Ala Ala Lys Ala Ala Ala Ala Ala Ala Ala Arg Lys Lys
 1               5                  10                  15

Ala Ala Lys Ala Ala Ala Ala Ala Ala Arg Lys Lys Ala Ala Lys Ala
            20                  25                  30

<210> SEQ ID NO 48
<211> LENGTH: 22
<212> TYPE: PRT
<213> ORGANISM: Artificial Sequence
<220> FEATURE:
<223> OTHER INFORMATION: protein fragment

<400> SEQUENCE: 48

Ala Arg Lys Lys Ala Ala Lys Ala Arg Lys Lys Ala Ala Lys Ala Arg
 1               5                  10                  15

Lys Lys Ala Ala Lys Ala
            20

<210> SEQ ID NO 49
<211> LENGTH: 24
<212> TYPE: PRT
<213> ORGANISM: Artificial Sequence
<220> FEATURE:
<223> OTHER INFORMATION: protein fragment

<400> SEQUENCE: 49

Ala Arg Lys Lys Pro Ala Lys Ala Ala Arg Lys Lys Pro Ala Lys Ala
 1               5                  10                  15

Ala Arg Lys Lys Pro Ala Lys Ala
            20

<210> SEQ ID NO 50
<211> LENGTH: 24
<212> TYPE: PRT
<213> ORGANISM: Artificial Sequence
<220> FEATURE:
<223> OTHER INFORMATION: protein fragment

<400> SEQUENCE: 50

Ala Arg Lys Lys Ala Ala Lys Ala Ala Arg Lys Lys Pro Ala Lys Ala
 1               5                  10                  15

Ala Arg Lys Lys Ala Ala Lys Ala
            20
```

```
<210> SEQ ID NO 51
<211> LENGTH: 24
<212> TYPE: PRT
<213> ORGANISM: Artificial Sequence
<220> FEATURE:
<223> OTHER INFORMATION: protein fragment

<400> SEQUENCE: 51

Ala Lys Lys Ala Arg Ala Ala Lys Lys Ala Arg Ala Ala Lys Lys Ala
 1               5                  10                  15

Arg Ala Ala Lys Lys Ala Arg Ala
            20

<210> SEQ ID NO 52
<211> LENGTH: 6
<212> TYPE: PRT
<213> ORGANISM: Artificial Sequence
<220> FEATURE:
<223> OTHER INFORMATION: protein fragment

<400> SEQUENCE: 52

Pro Arg Arg Leu Arg Leu
 1               5

<210> SEQ ID NO 53
<211> LENGTH: 6
<212> TYPE: PRT
<213> ORGANISM: Artificial Sequence
<220> FEATURE:
<223> OTHER INFORMATION: protein fragment

<400> SEQUENCE: 53

Thr Arg Arg Phe Arg Asp
 1               5

<210> SEQ ID NO 54
<211> LENGTH: 18
<212> TYPE: PRT
<213> ORGANISM: Artificial Sequence
<220> FEATURE:
<223> OTHER INFORMATION: protein fragment

<400> SEQUENCE: 54

Ala Arg Arg Ala Lys Ala Ala Arg Arg Ala Lys Ala Ala Arg Arg Ala
 1               5                  10                  15

Lys Ala

<210> SEQ ID NO 55
<211> LENGTH: 24
<212> TYPE: PRT
<213> ORGANISM: Artificial Sequence
<220> FEATURE:
<223> OTHER INFORMATION: protein fragment

<400> SEQUENCE: 55

Ala Arg Arg Arg Ala Ala Arg Ala Ala Arg Arg Ala Ala Arg Ala
 1               5                  10                  15

Ala Arg Arg Arg Ala Ala Arg Ala
            20
```

```
<210> SEQ ID NO 56
<211> LENGTH: 24
<212> TYPE: PRT
<213> ORGANISM: Artificial Sequence
<220> FEATURE:
<223> OTHER INFORMATION: protein fragment

<400> SEQUENCE: 56

Ala Lys Ala Ala Lys Lys Arg Ala Ala Lys Ala Ala Lys Lys Arg Ala
 1               5                  10                  15

Ala Lys Ala Ala Lys Lys Arg Ala
            20

<210> SEQ ID NO 57
<211> LENGTH: 27
<212> TYPE: PRT
<213> ORGANISM: Artificial Sequence
<220> FEATURE:
<223> OTHER INFORMATION: protein fragment

<400> SEQUENCE: 57

Ala Lys Arg Lys Lys Ala Ala Lys Ala Ala Lys Arg Lys Lys Ala Ala
 1               5                  10                  15

Lys Ala Ala Lys Arg Lys Lys Ala Ala Lys Ala
            20                  25

<210> SEQ ID NO 58
<211> LENGTH: 21
<212> TYPE: PRT
<213> ORGANISM: Artificial Sequence
<220> FEATURE:
<223> OTHER INFORMATION: protein fragment

<400> SEQUENCE: 58

Ala Arg Lys Lys Ala Ala Lys Ala Arg Lys Lys Ala Lys Ala Arg Lys
 1               5                  10                  15

Lys Ala Ala Lys Ala
            20
```

PEPTIDES MODULATING ACTIVITIES OF HEPARIN OTHER GLYCOSAMINOGLYCANS OR PROTEOGLYCANS

CROSS REFERENCE TO RELATED APPLICATIONS

This application claims priority in part under 35 U.S.C. §119 based upon U.S. Provisional Patent Application No. 60/118,276, filed Feb. 2, 1999.

This invention was made in part with government support from the National Institutes of Health Heart, Lung, and Blood Institute, grant numbers HL 53590 and HL29282 awarded by the National Institutes of Health. The government has certain rights in the invention.

FIELD OF THE INVENTION

The present invention generally relates to the field of peptide chemistry and to compositions of matter comprising peptides of various sequences and sizes and to methods of using said peptides with a strong affinity for glycosaminoglycans and proteoglycans, and more particularly to the various methods of using said peptides of various sequences and sizes as described below, wherein said peptides interact strongly with heparin, other glycosaminoglycans, or proteoglycans (PGs).

BACKGROUND OF THE INVENTION

Glycosaminoglycans (GAG)s modulate enzyme activities (e.g., of antithrombin III or heparin cofactor II), regulate cell behaviors (e.g., cell adhesion, growth, and differentiation), and control the function of extracellular matrices (e.g., diffusion of ions through basement membranes, and fibrillogenesis and lateral associations of collagens), largely through non-covalent interactions with proteins. (Jackson, R. L., et al., *Physiol Rev* 71:481–539, 1991; Lindahl, U. and M. Hook, *Ann Rev Biochem* 47:385–417, 1978). Although many proteins exhibit high affinity interactions with heparan sulfate or heparin and other GAGs, the specificity of such interactions has been defined for only a small number of them. (San Antonio, J. D. and R. V. Iozzo, *Encycl Life Sci* In Press, 2000). As heparan sulfates and heparin are among the most structurally diverse and biologically active of GAGs, their protein-interactive features have been the most thoroughly studied. Fine structural features of heparan sulfate chains, including defined sequences, rare modifications, domain structures, and gross polymer characteristics are each believed to contribute to various classes of interactions with different proteins. (San Antonio, J. D., and R. V. Iozzo, *Encycl Life Sci* In Press, 2000). For proteins, domains rich in basic amino acids appear to be necessary to facilitate interactions with GAGs; and for a subset of these proteins, potential heparin-binding consensus sequences have been described. (Cardin, A. D. and H. J. R. Weintraub, *Arteriosclerosis*, 9:21–32, 1989; Jackson, R. L., et al., *Physiol Rev* 71:481–539 1991).

Heparin-binding consensus sequences were discovered by Cardin and Weintraub, who surveyed amino acid sequences of known heparin-binding proteins, where they identified two potential consensus sequence motifs for heparin-binding, X-B-B-X-B-X or X-B-B-B-X-X-B-X, where X represents a hydropathic or uncharged amino acid, and B a basic amino acid. (Cardin, A. D. and H. J. R. Weintraub, *Arteriosclerosis* 9:21–32, 1989). For example, such consensus sequences were identified in proteins including apolipoprotein B-100, apo E, and vitronectin, to name a few. (See Cardin and Weintraub, 1989, for review). Molecular modeling of these consensus sites predicts the arrangement of amino acids into either α-helices or β-strands. This allows for the clustering of noncontiguous basic amino acids on one side of the helix, thus forming a charged domain to which GAGs could bind. Indeed, for some heparin-binding proteins, disruption of the heparin-binding consensus sequences hinders heparin binding. For example, chemical modification of the heparin-binding consensus site in thrombospondin (Lawler, J. and R. O. Hynes, *Cell Biol* 103:1635–1648, 1986) or site-directed mutagenesis of a heparin-binding sequence in fibronectin (FN) (Barkalow, F. J. B. and J. E. Schwarzbauer, *J Biol Chem* 266:7812–7818, 1991) eliminates or diminishes heparin-binding affinity. On the other hand, peptide mimetics of proposed heparin binding consensus sequences often fail to reveal the high affinities demonstrated by the native heparin-binding proteins. (Conrad, H. E, *Heparin-Binding Proteins*. Academic Press, 1998). Proteins often contain multiple, distal heparin-binding sequences that may come into proximity upon protein folding or multimerization, hence enabling binding through cooperativity. It has thus been speculated that the three dimensional arrangement of multiple heparin-binding consensus sites within or between heparin-binding proteins, and/or the presence of novel heparin-binding sites may be responsible for high affinity heparin- or HS-interactions with native proteins. Others have proposed a necessary approximately 20 Å distance between basic amino acids for heparin binding, regardless of protein tertiary structure. (Margalit, H., et al., *J Biol Chem* 268:19228–19231, 1993). Other heparin-binding sequences have been proposed that are variations of those reported by Cardin and Weintraub. The sequence TXXBXXTBXXXTBB, where T is a turn, was identified as a heparin-binding sequence in acidic FGF and bFGF. (Hileman, R. E., et al., *BioEssays* 20:156–167, 1998). X-ray crystallography revealed that this peptide backbone loops back upon itself in three turns to form a positively charged triangular heparin-binding pocket. The heparin-binding domain of von Willebrand factor resembles the motif XBBXXBBBXXBBX, a palindromic sequence in which the spacing and clustering of basic residues is important for heparin binding. (Sobel, M., et al., *J Biol Chem* 267:8857–8862, 1992). A third novel sequence has been demonstrated to be sufficient for weak heparin-binding in thrombospondin: WSXW. (Guo, N. H., et al., *J Biol Chem,* 267:19349–19355, 1992). However, for high affinity binding, this sequence must be flanked by basic residues. Other proteins including type I collagen (Sweeney, S. M., et al., *PNAS* 95:7275–7280, 1998), type VI collagen (Specks, U., et al., *EMBO J,*:4281–4290, 1992), extracellular-superoxide dismutase (Sandstrom, J., et al., *J Biol Chem,* 267:18205–18209, 1992), and mast cell chymases (Matsumoto, R., et al., *J Biol Chem,* 270:19524–19531, 1995), bind heparin via highly-basic binding regions which do not conform to any consensus sequence. In fact, in certain proteins, domains rich in basic amino acids have sometimes been shown to be unimportant for heparin binding. For example, the two heparin-binding consensus sequences identified in the FGFs were shown not to mediate heparin-binding (Wong, P., et al., *J Biol Chem,* 270:25805–25811, 1995; Thompson, L. D., et al., *Biochem,* 33:3831–3840, 1994). Therefore, there are likely other as yet undefined protein characteristics that must confer heparin-binding potential. Of relevance is the recent use of phage display technology to identify such novel heparin-binding sequences. This approach has generated three distinct HSPG-binding antibodies (van Kuppevelt, T. H., et al., *J*

Biol Chem, 273 21:12960–12966, 1998). Significantly, one of the sequences (GRRLKD, SEQ. ID. NO:1) contained a heparin-binding consensus sequence, while the others (SLRMNGCGAHQ, SEQ. ID. NO:2, and YYHYKVN, SEQ. ID. NO:3) did not. The latter two lack significant basic charge, and thus may bind HSPGs through non-ionic interactions. All three anti-HS antibodies showed specificity for heparin and HS but not for other GAGs. Additionally, the antibodies all reacted differently towards HS from various sources, which would suggest a specificity in recognition of discrete HS molecules.

GAG structure may also play a role in determining binding affinity and selectivity for proteins. A classic example is the antithrombin-binding site on heparin, which is present on only about one third of heparin chains (Lam, L. H., et al., *Biochem Biophys Res Commun*, 69:570–577, 1976), but which has a thousand-fold greater affinity for antithrombin III than the overall heparin structure (Lee, M. K., and A. D. Lander, *Proc. Nat Acad Sci USA*, 88:2768–2772, 1991). Several other sequences or structural motifs have been identified in HS GAGs which underlie their binding interactions with basic fibroblast growth factor (bFGF) (Maccarana, M., et al., *J Biol Chem*, 268:23898–23905, 1993), lipoprotein lipase (Parthasarathy, N., et al., J Biol Chem, 269:22391–22396, 1994), and interleukin-8 (Lindahl, U., et al., *J Biol Chem*, 273:24979–24982, 1998). Other aspects of GAG fine structure also contribute to specific interactions with proteins. For example, for short basic peptides, heparin displays high affinities for sequences with contiguous clusters of basic amino acids, whereas HS displays high affinities for those sequences in which clusters of basic amino acids are separated by non-basic residues (Fromm, J. R., et al., *Arch Biochem Biophys* 343 (1):92–100, 1997). Such binding preferences may relate to the increased spacing between sulfates found throughout HS as compared with the more densely sulfated heparin. Heparin is capable of binding to a wide array of proteins, due to its high degree of flexibility and ability to "fit" itself into proteins.

Because of the presence of heparin-binding sequences in many physiologically important proteins, there was a need for small peptides with high affinities for heparin, or for heparin-like molecules (i.e., PGs, or other GAGs), to use in a variety of applications to modulate the activities of native GAGs and PGs. Therefore, in the present invention peptides with high affinities for heparin or for PGs have been designed to include heparin-binding consensus sequences; however, in doing so it was necessary to take into account previous studies showing that short peptides of native proteins do not behave like the native proteins, due to conformation and size limitations, and a lack of cooperativity in binding to various ligands. Thus, peptides were also designed including multiple consensus sequences arranged in tandem: $(X-B-B-X-B-X)_n$ or $(X-B-B-B-X-X-B-X)_m$, where n=1–6, and m=1–5.

The basis for the design of the peptides of the present invention is the inclusion in their structure of multiple copies of sequences (including XBBXBX or XBBBXXBX, where X is a hydropathic amino acid and B is a basic amino acid), representing consensus sequences for heparin or PG-binding in natural proteins, and, in addition, may include the presence of a single cysteine residue preferably occupying, but not limited to, a position within a three residue distance of either the C- or N-peptide terminus, that promotes peptide dimer formation and greatly enhances peptide binding interactions with heparin. Any of these peptides may also be constructed of either L- or D-, or combinations of L- and D-amino acid isomer forms, or containing any amino acid in the X position of any peptide. Any of these peptides may also be used as carriers and/or integral components of various pharmaceuticals or bioactive agents targeted to interact with cell surfaces expressing PGs or heparin-like molecules, or to tissues which express PGs as cell surface or extracellular matrix components.

Current approaches to design peptides which bind to heparin include Wakefield et al. (U.S. Pat. No. 5,534,619, and U.S. Pat. No. 5,919,761; Wakefield, T. W., et al.,*J. Surg. Res.*, 56:586–593 1994; Wakefield, T. W., et al., *J. Surg. Res.*, 63:280–286, 1996) and Harris et al. (U.S. Pat. No. 5,877,153). The Wakefield peptide sequences, specifically the grouping and spacing of the basic amino acids, are patterned after naturally-occurring protamines. The Harris et al. peptides are a series of single-chain and multi-chain peptides which incorporate arginines within a backbone of alanines. The spacings of the arginines are based on the heparin-binding sequence of antithrombin III. All the Harris peptides have AE as their N-terminal amino acid sequence.

The present invention, however, includes peptides based on the consensus sequences (XBBXBX) and (XBBBXXBX) determined by the analysis of a wide range of known heparin-binding proteins by Cardin et al (Cardin, A. D., and H. J. R. Weintraub, *Arteriosclerosis*, 9:21–32, 1989). The peptides designated in this application consist of as many as 6 repeating units of these sequences. These sequences are not found in protamine. In contrast to Wakefield et al., the peptides of the present invention contain repeating motifs with groups of two and 1 basic residues separated by a single alanine, or three and one basic residues separated by alanine-alanine. While single copies of these general sequences are associated with the heparin binding sites in many proteins, peptides derived from these proteins which include single copies of these sequences and their native surrounding amino acids have insignificant binding affinities for heparin. Furthermore, some proteins contain the Cardin type consensus sequences, but these sequences were shown not to bind heparin, and many other proteins bind heparin yet do not contain such consensus sequences. Thus it is not intuitive to use these types of sequences as heparin-binding agents.

Furthermore, the sequences used by Harris et al. mimic those found in a naturally occurring protein in terms of spacing and grouping of the basic residues, with no internal repeating structures, but the single-chain peptides have relatively weak ability to interact with heparin. Substantial binding is found only when multi-chain structures are formed. In contrast, the present invention involves, for the most part, single-chain peptides with repeating Cardin sequences. These peptides have a strong capability for binding to both unfractionated heparin and low molecular weight heparin.

A further difference between the peptides in the Wakefield and Harris patents resides in the engineering of alpha-helical structure into the peptides. Some of their peptides have partial alpha-helical structure. In the present invention, peptides are not alpha-helical in the native state, but assume an alpha-helical conformation when bound to heparin. Thus, the peptides of the present invention may have more flexibility to conform to a variety of heparin sequences encountered in any of the therapeutic heparin formulations.

An additional aspect of the present invention is the N-terminal-peptide sequences of the proteoglycan serglycin, which contain a single full or partial Cardin site near the N-terminus and a cysteine residue three amino acids from the C-terminus. These peptides dimerize through their cysteine residues and thus form a strong heparin-binding unit. Another feature of the present invention is the inclusion of cysteines near the C-termini of all the Cardin site peptides and the serglycin peptides to further enhance their heparin-binding functions.

The peptides of the present invention have a number of uses. One method of using these peptides is to promote cell attachment or adhesion to natural or synthetic surfaces.

Vascular diseases such as atherosclerosis, restenosis, and aortic aneurysms often result in permanent damage to blood vessels; typically, vessels become occluded as a result of vascular insult, causing decreased blood flow (Robbins, S. L. and R. S. Cotran, Pathological Basis of Disease. W. B. Saunders, Philadelphia. 598–613 pp., 1979). One approach to treatment of damaged vessels is surgical replacement of the diseased segment with an autologous or non-autologous native tissue graft (Zarge, J. I., et al., In *Principles of Tissue Engineering*, R. P. Lanza, et al., editors. Academic Press, Austin, 349–364, 1997). This approach is limited in that either healthy vessels must be removed (autologous) or a suitable donor vessel must be available (non-autologous). An alternative approach is the use of a synthetic vascular graft in place of a native tissue graft. In addition to not requiring an appropriate donor vessel or the removal and transplantation of a non-diseased vessel to the diseased area, synthetic vascular grafts can be modified to reduce complications from immune rejection or to increase patency rates and graft success (Munro, M. S., et al., *Trans Am Soc Artif Intern Organs,* 27:499–503, 1983; Leikweg, W. G., and L. J. Greenfield, *Surg,* 81:335–342, 1977; Park, K. D., et al., J Biomed Mater Res, 22:977-9227–29, 1988).

Historically, inert polymers composed of terephthalate (Dacron) or of expanded polytetrafluoroethylene (ePTFE) have been used to construct prosthetic vascular grafts (Zarge, J. I., H. P., and H. P. Greisler, In Principles of Tissue Engineering, R. P. Lanza, et al., editors. Academic Press, Austin, 349–364, 1997), but these materials typically invoke an immune response. Synthetic grafts can react with serum proteins and blood cells that can promote thrombus formation and lead to pseudointimal hyperplasia. (Zarge, J. I., H. P., and H. P. Greisler, *In Principles of Tissue Engineering*, R. P. Lanza, et al., editors, Academic Press, Austin, 349-364, 1997). Vascular replacement has been limited to large or medium size arteries where blood flow rates are high, outflow resistance is low, and as a consequence, the graft is less likely to become occluded by a thrombus. Conversely, small arteries are more prone to graft failure via thrombosis or hyperplasia because of lower flow rates and higher outflow resistance. An inappropriate infiltration of smooth muscle cells during the healing process can also result in vessel occlusion. Control of this immune response and smooth muscle cell infiltration could occur in a vessel lined with endothelial cells, which secrete factors inhibiting platelet and erythrocyte aggregation (Fantone, J. C., and P. A. Ward, In *Pathology*, E. Rubin, and J. L. Farber, editors. J. B. Lippincott Co., Phil. 43, 1994), as well as factors that inhibit smooth muscle cell proliferation, but, endothelial cells typically fail to proliferate well on these graft materials. (Zarge, J. I., H. P., and H. P. Greisler, In *Principles of Tissue Engineering*, R. P. Lanza, et al., editors, Academic Press, Austin, 349-364, 1997). Attempts have been made to overcome these limitations by coating the graft with anticoagulants to limit thrombus formation, growth factors to promote endothelial cell proliferation, or proteins with antiproliferative effects on smooth muscle cells. The presence of endothelial cells in the transplanted graft, however, is thought to increase the chance of survival of the graft (Herring, M. B., et al., *Surgery.* 84:498, 1978). Studies in which prosthetic vascular surfaces were seeded with autologous endothelial cells before transplantation displayed an increase of 30% in patency rates over three years in comparison to non-seeded surfaces (Zilla, P., et al., *J Vasc Surg,* 19:540–548, 1994). The obvious limitation of pre-seeding, however, is the need to harvest and culture endothelial cells to the appropriate density prior to seeding, as well as generating vascular graft materials with surface properties optimized for endothelial cell attachment and proliferation.

Endothelial cells carry a negative surface charge (Vargas, F. F., et al., *Membrane Biochemistry.* 9:83, 1990) that can inhibit platelet adherence, and they express a variety of GAGs on their surface that bind the anti-coagulant antithrombin III (Mertens, G., et al., *J Biol Chem,* 267 (28): 20435–20443, 1992). Vargas and co-workers have shown that sulfated GAGs are the main carriers of surface charge on vascular endothelial cells, primarily as heparan sulfate (HS) and chondroitin sulfate PGs (Vargas, F. F., et al., *Membrane Biochemistry.* 9:83, 1990). Specific types of PGs on endothelial cell surfaces include the syndecans and glypican (Mertens, G., et al., *J Biol Chem,* 267 (28): 20435–20443, 1992).

Thus, the surface chemistry (i.e., the predominance of its PG component) of endothelial cells will prove useful as a means of tethering and maintaining these cells in a transplanted synthetic vascular graft. One goal of the present invention is to discover peptides with high affinities for endothelial cell surface PGs. Such peptides are used by covalently attaching them to synthetic vascular grafts, and in the presence of endothelial cells, promote their attachment to the graft surface, thereby increasing the probability of graft success.

Another use of the peptides of the present invention is for heparin-and PG-binding as modulators of hemostasis via interactions with endothelial cells and as anti-heparin therapy in plasma. These peptides of the present invention function as agents for neutralization of unfractionated heparin, low molecular weight heparin, or Orgaran (Organon, mixture of chondroitin sulfate/heparan sulfate/dermatan sulfate) overdose.

Currently, the only FDA-approved heparin antidote available is Protamine. Protamine can cause several serious side effects in patients, and although Protamine is effective in humans against unfractionated heparin, it is not effective against low molecular weight heparins or against Orgaran. Since Protamine is a natural product that is an undefined mixture of amino acids, its content is variable across different preparations, and thus dosage is uncertain, presenting problems in its clinical use.

The peptides of the present invention are useful for counteracting the actions of heparin and other anticoagulant glycosaminoglycans on thrombin and Factor Xa activity, and may affect other proteins as well. Heparin is used routinely for anticoagulation. The interactions of exogenously administered heparin with the proteins of the coagulation and fibrinolytic pathways have been summarized in detail (Conrad, H. E., Heparin-Binding Proteins, Academic Press, San Diego, 1998). These interactions are complex on many levels. The best-characterized targets for heparin are the procoagulant proteins thrombin and Factor Xa, which are inhibited by AT III when heparin binds to AT III. However, heparin acts at many sites. In some cases, the effect of heparin is anticoagulant and in other cases procoagulant. Some proteins, e.g. AT III, have heparin-binding consensus sites. However, the putative heparin-binding sequences are different for every known protein in these pathways, and the effects may depend on the 3-dimensional relationships of basic residues resulting from protein folding, rather than a short linear sequence, as is known for the binding of heparin to AT III (Carrell, R. W., et al., *Structure* 2:257–270, 1994). A tetrameric protein conformation of platelet factor 4 (PF4) is required for long-chain heparin binding (Rucinski, B., et al, *Thromb Hemostas* 63:493–498, 1990; Ibel, K., et al, *Biochim Biophys Acta* 870:58–63, 1986; Talpas, C. J., et al, *Biochim Biophys Acta* 1078:208–218, 1991). Formation of a two-protein complex (PAI-1/vitronectin) involves the vitronectin heparin binding site (Kost, C. W. et al, *J Biol Chem* 267:12098–12105, 1992; Deng, G., et al, *J Cell Biol* 134:1563–1571, 1996) and therefore could be disrupted by heparin. The inactivated AT III/thrombin complex is released from the endothelial surface, binds as a complex to vitronectin, and then is taken up for catabolism by binding of the vitronectin heparin-binding domain to HSPG on the endothelium (Hogasen, J., et al, *J Biol Chem* 267:23076–23082, 1996; deBoer, H., et al, *J Biol Chem* 94:1279–1283, 1993).

Heparin is a complex mixture of polysaccharides. Some of the interactions require long-chain heparins (AT III for inactivation of thrombin and binding to thrombin, HC II, PF4, and thrombospondin) while others depend on or can function with low molecular weight heparin chains (AT III for inhibition of Factor Xa, vitronectin, TFPI) (Conrad, H. E., Heparin-Binding Proteins, Academic Press, San Diego, 1998). To further complicate the situation, specific sequences within the heparin chains may be required for interactions with the different proteins (Conrad, H. E., Heparin-Binding Proteins, Academic Press, San Diego, 1998), and all naturally-occurring heparins and heparan sulfates are very diverse in their carbohydrate structures. The catabolism of the higher molecular weight heparins in the plasma results in a constantly changing spectrum of actual heparin chains that are available for reaction with the various proteins, and thus the nature of the possible anticoagulation or fibrinolytic reactions will change over the hours after the dosage is given. Finally, many other plasma proteins that are not involved in the coagulation or fibrinolytic processes can bind heparin, and variations in the concentration and nature of these proteins in different individuals can influence the availability of heparin for these two pathways. Thus specific single peptides or combinations of peptides may target specific interactions between heparins and cell surface or plasma proteins to get the greatest effectiveness and minimize adverse reactions It is often necessary to reverse the effects of heparin when anticoagulation has reached a stage at which hemorrhage becomes a threat, notably after the routine use of heparin for anticoagulation during cardiopulmonary bypass, and in patients who develop an endogenous heparin-like coagulation inhibitor. The most commonly used anti-heparin drug is protamine, a mixture of basic proteins from fish sperm nuclei, that contains a high concentration of the amino acid arginine. When injected into a person who has been treated with heparin, it complexes rapidly to the heparin, thereby neutralizing its activity. Protamine also has numerous side effects including pulmonary hypotension that are difficult to control and provide significant health risks to the patient. Also, since Protamine is a poorly-defined and potentially variable product, dosage determination can be problematic. Importantly, Protamine has been shown to be ineffective for neutralization of low molecular weight heparins and the non-heparin glycosaminoglycan anticoagulant Orgaran.

Well-defined heparin-or other GAG-binding peptides could be of considerable utility for reversing overdose of these specific anticoagulant preparations. Carson and co-workers (Lui, S., et al, *J Biol Chem* 94:1739–1744, 1997) have identified a heparin-binding peptide from an epithelial/endothelial cell surface protein that has some ability to neutralize heparin effects on thrombin generation, but optimal effects were found only at high peptide concentrations and low heparin and low thrombin concentrations. Preliminary data in the present invention suggest that the Cardin and serglycin peptides reverse the heparin effect on thrombin at several-fold lower peptide concentrations and 7-fold higher thrombin concentrations than the peptide described by Carson and co-workers. We have also shown that several of the peptides are effective neutralizers of low molecular weight heparin (Enoxaparin, Lovenox) and Orgaran in vitro, and of Lovenox in vivo in rats, in accordance with their affinity constants for low molecular weight heparin in vitro. Thus the peptides described in this application may have important clinical applications, especially if they can be targeted to specific reactions in the relevant pathway and to specific classes of heparins.

Another use for the peptides of the present invention is to block the uptake and clearance of heparin by blocking uptake receptors on tissue, without binding to the circulating heparin itself, and thus prolonging the half-life in the circulation. Such an agent would reduce the frequency of administration of the drug, as well as the amount needed. This could be especially useful for home-based therapy with low molecular weight heparin, which is administered by subcutaneous injection and is becoming the standard for post-hospitalization anticoagulation.

Multiple interactions between the proteins of the coagulation and fibrinolysis pathways and endothelial cell surface PGs generate a complex surface on which ongoing coagulation and fibrinolysis are normally balanced to create a non-thrombotic state. The heparan sulfate PGs (HSPGs) of the endothelium mediate antithrombotic/anticoagulant function through binding and activation of Antithrombin III (AT III) and binding of tissue factor pathway inhibitor (TFPI). AT III bound to endothelium heparan sulfate can inactivate both thrombin and Factor Xa. TFPI binds to Factor Xa and this complex then interacts with the Factor VIIa/tissue factor complex to inactivate both Factors VIIa and Xa. Adherence of TFPI to the endothelium via the HSPG protects against proteolysis of the heparin-binding C-terminal domain (Nordfang, O., et al, *Biochem.* 30:10371–10376, 1991); without this domain, activity is lost. Heparin-binding peptides such as those described in this study could behave similarly to platelet factor 4 (PF4) in that they could bind to the heparan sulfates on the endothelial surface. For example, docking of a peptide onto the heparan sulfate chain in a reversible manner could protect the GAG from degradation by platelet heparitinase released by aggregating platelets at the site of a developing thrombus, leaving the GAG able to resume its antithrombotic function in a shorter time frame than would be required for resynthesis. On the other hand, a peptide with a very high affinity for the AT II-binding sequences of endothelial heparan sulfate could block the binding and therefore the activity of AT III and provide a more favorable surface for clot formation, thus promoting wound healing.

Therefore, in some embodiments, the peptides of the present invention have affinity for heparin/heparan sulfate on cell surfaces and can be used as agents to promote healing, either by injection or by topical application. Injection or topical application of the peptides alone also might serve to assist wound-healing by dislodging ATIII and/or tissue factor pathway inhibitor (TFPI) from their binding sites and subsequently blocking these binding sites on the endothelium of broken blood vessels, thereby reducing the anticoagulant activity of the surface and enabling a clot to form. Alternatively, contemporaneous injection or application of a mixture of heparin and a heparin-binding peptide could generate a molecular complex, or low affinity heparin sink, that will then transfer the heparin to proteins with greater heparin-binding affinities.

The peptides of the present invention can be used to bind and neutralize or activate, or otherwise modulate the actions of various PGs or GAGs, thereby influencing their growth- or differentiation-modulating activities. For example, heparin and heparin-like molecules such as cell surface HSPGs are known to inhibit smooth muscle cell proliferation, to potentiate the activities of growth factors like basic or acidic fibroblast growth factor on endothelial cells, and to inhibit or promote cell differentiation of smooth muscle cells, chondrocytes, and other cell types. The peptides described here could be used to modulate the actions of heparin or endogenous heparan sulfate PGs, with significant consequences to cell growth and differentiation.

GAGs exhibit a wide variety of potent activities on cell growth, migration, differentiation, metabolism, and adhesion (Jackson, R. L., et al., *Physiol Rev,* 71:481–539, 1991; San Antonio, J. D., and R. V. Iozzo, *Encylc Life Sci,* In Press, 1999). One of the earliest reports of an effect of GAGs on cell growth reported that fibroblastic mouse L cells in suspension culture exposed to 50 μg/ml heparin were growth inhibited by seventy-three percent (Karnovsky, M. J., et al., *Annals of the New York Academy of Science,* 556:268–281, 1989). Several strong antiproliferative activities of GAGs on a variety of cell types have been reported since (San Antonio, et al., *Connective Tissue Res,* 37:87–103, 1998). The effects of heparin on vascular smooth muscle cells (VSMC) have been the most extensively studied owing to the relevance of this topic to vascular disease. Although for some cell types heparin antiproliferative action may involve displacement of HS or heparin-binding growth factors from cell surface receptors, for VSMC heparin may also be internalized and act directly in the cytoplasm and nucleus (Karnovsky, M. J., et al., *Annals of the New York Academy of Science,* 556:268–281, 1989). An important component of vascular diseases including atherosclerosis and restenosis is the pathological growth of vascular smooth muscle cells. As GAGs are strong regulators of VSMC growth they are potentially useful in treating these diseases. The effect of heparin on VSMC growth in vivo was first discovered in experiments aimed at determining whether heparin may inhibit the response to injury cascade of accelerated atherosclerosis owing to its antithrombotic activity; a dramatic inhibition of VSMC proliferation by heparin was observed (Karnovsky, M. J., et al., *Annals of the New York Academy of Science,* 556:268–281, 1989). It was next shown that the growth effect of heparin on VSMC in vivo is exhibited by either anticoagulant or non-anticoagulant fractions, and that these effects are mimicked by heparin or HS on VSMC in vitro (Karnovsky, M. J., et al., *Annals of the New York Academy of Science,* 556:268–281, 1989). It has been proposed that in the healthy vascular wall, endothelial-derived HS maintains VSMC in a quiescent growth state, but that injuries which result in endothelial denudation remove this paracrine mechanism, resulting in uncontrolled VSMC proliferation and vascular lesion formation (Karnovsky, M. J., et al., *Annals of the New York Academy of Science,* 556:268–281, 1989). Thus, the peptides described here are useful in neutralizing the antiproliferative activities of endogenous or exogenous heparins or heparan sulfates on vascular smooth muscle cells or other cell types. For example, the peptides may be used to neutralize endothelial cell-derived HSPG's during vascular wound healing.

Heparins and heparan sulfates have been shown to promote cartilage development at low concentrations, and to inhibit it at high concentrations (San Antonio, J. D., et al., *Devel Biol,* 123:17–24, 1987). Thus, the peptides described here may prove useful as modulators of cartilage differentiation, especially in instances where cartilage tissue scaffolds are being constructed for autologous tissue transplants, e.g., for use in orthopedic surgical applications.

Tumor matrix stromas may play important roles in potentiating tumor growth and metastasis (Iozzo, R. V., *Lab Invest,* 73:157–160, 1995). For example, increases in perlecan expression are seen during development of colon carcinomas and of malignant melanomas; its HS chains may potentiate growth factor activity and induce angiogenesis surrounding the tumor, thereby enhancing its growth (Nugent, M., and R. V. Iozzo, *Internat J Biochem. and Cell Biol,* In Press, 1999). Furthermore, the binding selectivity of HS chains for various members of the fibroblast growth factor family can be influenced by fine structural features such as the patterns of 6-O-sulfation and the abundance of sulfated domains (Lindahl, U., et al., *J Biol Chem,* 273:24979–24982, 1998). A pathological role of tumor cell surface PGs has also been suggested. For example, Chinese hamster ovary cells carrying various mutations of PG synthesis were injected into nude mice and tested for their tumorigenic abilities. Mutants which expressed low levels of PGs failed to produce tumors, and of those with normal PG levels but with defects in the synthesis of specific GAG types, the structure of HS, but not of CS, was most important to their tumorigenicity (Esko, J. D., et al., *Science,* 241:1092–1096, 1988). Thus, if the peptides described here exhibit GAG type specific or GAG sequence specific binding preferences, they may be useful in directly modulating the function of tumor cell GAGs or PGs, or as carriers of drugs to be targeted to control the growth of, or to kill tumor cells expressing unique GAGs or PG variants.

PGs secreted by normal cells are proposed to play a key barrier function by inhibiting the migration of tumor cells across basement membranes. However, tumor cells have been shown to secrete the enzyme heparatinase, which degrades the HS chains within basement membranes, thereby potentially enabling such malignant cells to breach the basement membrane, enter the circulation, and spread throughout the body (Katz, B. Z., et al., *Invasion and Metastasis,* 14:276–289, 1994–5). The peptides described here could thus be used as inhibitors of GAG hydrolase-mediated tumor metastasis.

Another key component of tumor growth and survival is proposed to be the development of a blood vessel supply to the tumor (Folkman, J., and M. Klagsburn, *Science,* 235:442–447, 1987). Tumor angiogenesis is strongly inhibited by the heparin-binding protein endostatin (O'Reilly, M. S., et al., *Cell.* 88 (7):277–285, 1997), and in vitro, heparin is required to promote angiogenesis in response to growth factors (Jackson, C. J., et al., *Exp Cell Res,* 215:294–302, 1994). The peptides described here could therefore function as inhibitors of growth-factor dependent angiogenesis in vivo, therefore inhibiting tumor growth.

Yet another application of the present invention is the targeting of drugs to cell surfaces of endothelium or other cell types which express PGs. For example, drugs to be targeted to endothelial cells could be complexed with the peptides described here, or the peptide sequences could be integrated into the drug, and then the drug could be administered to the systemic circulation. The peptide component of the drug would mediate high affinity interactions with the endothelial cell surface, effectively delivering the drug for action at that site, or potentially promoting the cellular uptake of the drug.

Since endothelial cell surface charge is largely due to cell surface GAGs and PGs (Vargas, F. F., et al., *Membrane Biochemistry*, 9:8, 1990), and the peptides described in this patent exhibit high affinity interactions with endothelial cell PGs, then the peptides can be applied as tools to deliver drugs to endothelial cells in vivo. For example, a drug which is designed to act on endothelial cells could be complexed with the peptides either covalently or non-covalently, and delivered to the systemic circulation. The peptide component of the complex would facilitate high affinity interactions with the endothelial cell surface, thereby bringing the drug in contact with the endothelial cell surface to exert its activity there, or to facilitate its uptake by the endothelial cells. Such a use for these peptides is not limited to endothelial cells, since many cell types in the body express distinct classes or types of PGs. Furthermore, within each type of cell population, structural variants of GAGs and PGs may be expressed, thereby distinguishing these cell variants on a structural and functional level. Thus, for example, it has been shown that normal B cells and various transformed (cancerous) B cells express different variants of syndecan-1 which show distinct differences in the chemistry of their heparan sulfate chains (Sanderson, R. D., et al., *J Biol Chem*, 269:13100–13106, 1994). If some of the peptides described here show binding preferences for the heparan sulfates expressed on the cancerous B cells, then such peptides could be used as carriers of drugs targeted to those cells. Finally, another potential target cell for the peptides described here are the chondrocytes, which are present in all joint surfaces and which express high amounts of sulfated GAGs in their pericellular spaces. Previous work has shown that the basic endogenous protein lysozyme accumulates in joints, likely owing to its interactions with cartilage GAGs (Keuttner, K., et al., *Clin Orthop Relat Res*, 112:316–339, 1975). These results suggest that basic peptides such as those described here, when injected systemically or directly into or near joints, should also concentrate and/or be retained in cartilagenous regions. Therefore, systemic application of the peptides described here, complexed with drugs targeted to chondrocytes for treatment of, for example, arthritic diseases, could potentially find many uses.

Another application of the peptides of the present invention is their use to modulate the activities of enzymes that act on GAG substrates. For example, GAG hydrolases including some of the heparinases and heparatinases contain heparin-binding consensus sequences which they are proposed to use in binding to their GAG substrates. The peptides described here could be used to inhibit this binding through competition, thereby inhibiting the activity of the enzymes.

Several of the enzymes that hydrolyze heparin and heparan sulfates are used commonly in scientific investigations to characterize the structure and function of GAGs within tissue and cell preparations. Furthermore, these enzymes are important natural products as they are secreted by specific types of bacteria, are present in the venom of some poisonous snakes, and are secreted by normal human cells, and by human tumor cells, where they are proposed to promote tumor cell metastasis (Katz, B. Z., et al., *Invasion and Metastasis*, 14:276–289, 1994–5; Sasisekharan, R., et al., *Proc Natl Acad Sci USA*, 90:3660–3664, 1993). Since these enzymes contain heparin-binding consensus sequences that are proposed to mediate the interactions between the enzyme and their substrates, the peptides described here will serve as effective inhibitors of enzyme action for many in vitro and in vivo applications.

Yet another use of the peptides of the present invention is in the affinity purification of bioactive sequences of GAGs. For example, some heparin-binding proteins have been shown to interact with specific sequences or domain structural features on heparins or heparan sulfates, including antithrombin III, lipoprotein lipase, and laminin. Thus, the peptides described here may similarly exhibit binding preferences for distinct sequences in GAGs, making them useful as affinity matrices for the purification of specific GAG sequences for a variety of uses.

Heparin-binding proteins have been shown to interact with specific sequences or domain structural features on heparins or heparan sulfates, including ATIII (Lam, L. H., et al., *Biochem Biophys Res Commun*, 69:570–577, 1976), lipoprotein lipase (Parthasarathy, N., et al., *J Biol Chem*, 269:22391–22396, 1994), and laminin. For example, the determinant on heparin necessary for AT-Ill binding was located on only about one third of heparin chains, and is a pentasaccharide sequence composed of a 6-O-sulfated glucosamine in the first position, a 3-O-sulfated central glucosamine, two N-sulfated glucosamines, and a carboxylated iduronic acid (Jackson, R. L., et al., *Physiol Rev.* 71:481–539, 1991). To purify this sequence from heparin is an expensive endeavor as it requires heparin fragmentation followed by affinity chromatography on ATIII columns. However, if any of the peptides described here showed binding preference for specific sequences such as the ATIII binding site, then they could be used as low cost affinity matrices for the large scale purification of bioactive GAG sequences and fragments. Furthermore, such approaches could potentially be useful in endeavors to sequence or functionally characterize GAG samples of unknown chemistries, if libraries of heparin-binding peptides contain peptides with unique binding selectivities for distinct features of heparin or heparan sulfate chemistry, these could be used as tools fractionate, isolate, and quantitate specific GAG sequences from complex GAG mixtures.

DEFINITIONS

"Modulating" means binding, neutralizing, activating, or modulating.

SUMMARY OF THE INVENTION

The present invention generally relates to peptides of various sequences and sizes with a strong affinity for glycosaminoglycans and proteoglycans. The present invention also comprises the methods of using said peptides of various sequences and sizes, wherein said peptides interact strongly with heparin, other glycosaminoglycans, or proteoglycans (PGs).

Peptides of the present invention can be used to:
1. Promote cell attachment or adhesion to natural or synthetic surfaces. For example, a use of these peptides may include endothelialization of synthetic vein graft surfaces, which is known to increase the chances for the long term success of the vein graft. Thus, peptides can be covalently linked to synthetic or natural polymers used to construct vascular graft scaffolds, where they will interact strongly with endothelial cell surface PGs, thereby promoting endothelial cell attachment and thus graft colonization and success. Peptides could also be linked to synthetic tissue culture surfaces, to promote rapid and strong attachment of cells expressing PGs.

2. Bind heparin and PG to modulate hemostasis via interactions with endothelial cells and as anti-heparin therapy in plasma. These peptides function as agents for neutralization of unfractionated heparin, low molecular weight heparin, or Orgaran (Organon, mixture of chondroitin sulfate/heparan sulfate/dermatan sulfate) overdose.

3. Block the uptake and clearance of heparin by blocking uptake receptors on tissue, without binding to the circulating heparin itself, and thus prolonging the half-life in the circulation. Such an agent would reduce the frequency of administration of the drug, as well as the amount needed.

4. Counteract the actions of heparin and other anticoagulant glycosaminoglycans on thrombin and Factor Xa activity.

Figure 5A:
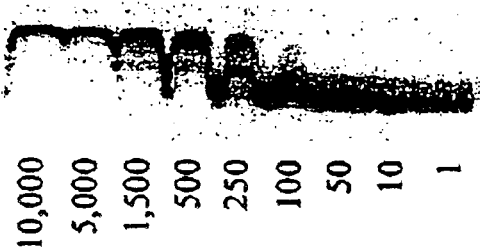
Figure 5A:
Figure 5B:
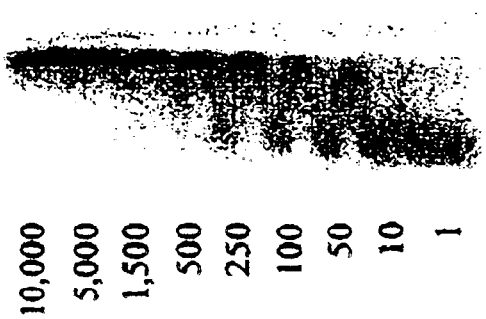

5. Agents to promote healing, by binding heparin/heparan sulfate on cell surfaces. The peptides could be administered either by injection or by topical application. In addition, contemporaneous injection or application of a mixture of heparin and a heparin-binding peptide could generate a molecular complex, or low affinity heparin sink, that will then transfer the heparin to proteins with greater heparin-binding affinities.
6. Bind and neutralize or activate, or otherwise modulate the actions of various PGs or GAGs, thereby influencing their growth- or differentiation-modulating activities. For example, heparin and heparin-like molecules such as cell surface HSPGs are known to inhibit smooth muscle cell proliferation, to potentiate the activities of growth factors like basic or acidic fibroblast growth factor on endothelial cells, and to inhibit or promote cell differentiation of smooth muscle cells, chondrocytes, and other cell types. The peptides described here could be used to inhibit the actions of heparin or endogenous heparan sulfate PGs, with significant consequences to cell growth and differentiation.
7. Neutralize the antiproliferative activities of endogenous or exogenous heparins or heparan sulfates on vascular smooth muscle cells
8. Modulate cartilage differentiation, especially in instances where cartilage tissue scaffolds are being constructed for autologous tissue transplants, e.g., for use in orthopedic surgical applications.
9. Modulate the function of tumor cell GA Gs or PGs, or as carriers of drugs to be targeted to control the growth of, or to kill tumor cells expressing unique GAGs or PG variants.
10. Inhibit GAG hydrolase-mediated tumor metastasis.
11. Inhibit growth-factor dependent angiogenesis in vivo, therefore inhibiting tumor growth.
12. Target drugs to cell surfaces of endothelium or other cell types which express PGs.
13. Modulate the activities of enzymes that act on GAG substrates.
14. Facilitate affinity purification of bioactive sequences of GA Gs.

BRIEF DESCRIPTION OF THE DRAWINGS

FIG. 1 Calculation of heparin-binding affinities of peptides containing heparin-binding consensus sequences. Retardation coefficients (R) for the migration of low $M_r$, $^{125}$I-tyramine-heparin through peptides were determined from ACE gel electrophoretograms, and are plotted against peptide concentration as detailed in Materials and Methods. Smooth curves represent non-linear least-squares fits to the equation $R=R_\infty/\{1+(K_d/[\text{peptide}])^n\}$. Peptides containing single consensus sequences (AKKARA, SEQ. ID. NO:4, -●- or ARKKAAKA, SEQ. ID. NO:5, -○-) do not bind heparin with a measurable affinity; in contrast, significant heparin-binding is seen with peptides containing multiple heparin-binding consensus sequences and increases as a function of peptide $M_r$. $(AKKARA)_2$ (SEQ. ID. NO:14), -X-, $K_d \cong 40$ μM; $(ARKKAAKA)_2$ (SEQ. ED. NO:6), -■-, $K_d \cong 6$ μM; $(AKKARA)_3$ (SEQ. ID. NO:7), -□-, $K_d \cong 2$ μM; $(ARKKAAKA)_3$ (SEQ. ID. NO:43), -▲-, $K_d \cong 135$ nM and $(ARKKAAKA)_4$ (SEQ. ID. NO:8), -Δ-, $K_d \cong 40$ nM.

FIG. 2 Calculation of heparin-binding affinities of SG peptides. R values for the migration of low $M_r$ $^{125}$I-tyramine-heparin through peptides containing sequences native to the mouse (YPARRARYQWVRCKP, SEQ. ID. NO:9, -○-) or human (YPTQRARYQWVRCNP, SEQ. ID. NO:10, -●-) SG PG core proteins were determined from ACE gel electrophoretograms as detailed in Materials and Methods. SG peptides displayed relatively strong affinities for heparin ($K_d \cong 200$ and 900 nM for the mouse and human peptides, respectively), in comparison to peptides of similar size which contain multiple repeats of heparin-binding consensus sequences [e.g. $(AKKARA)_3$ (SEQ. ID. NO:7) $K_d \cong 2000$ nM, $(ARKKAAKA)_2$ (SEQ. ID. NO:6) $K_d \cong 6000$ nM; Table I]. Peptide AAARRARAAAARAKA (SEQ. ID. NO:11), (-■-) displayed negligible heparin-binding affinity ($K_d \cong 75$ μM) indicating the importance of the non-basic residues to heparin-binding. YPARRARYQWVRCKP (SEQ. ID. NO:9)-heparin binding in the presence of β-ME (YPARRARYQWVRCKP, SEQ. ID. NO:9,+ β-ME, -X-), was decreased by over 20-fold ($K_d \cong 4$ μM). Replacement of cysteine by alanine in the mouse SG peptide (YPARRARYQWVRAKP, SEQ. ID. NO:12, -□-) further reduced heparin-binding affinity ($K_d \cong 36$ μM).

FIG. 3 CD spectroscopy of $(AKKARA)_6$ (SEQ. ID. NO:13) in the presence or absence of low $M_r$ heparin. CD spectra measurements of $(AKKARA)_6$ (SEQ. ID. NO:13) in the absence of heparin (1:0,-●-), reveals peaks at 195 nm and 216 nm and a crossover at 210 nm, indicative of an extended charged coil conformation. Upon heparin addition (1:0.25, -○-; 1:0.50, -X-), the peptide conformation is altered and at a 1:1 peptide-heparin ratio (-■-) the peptide becomes α-helical with characteristic α-helical peaks at approximately 190, 207, and 222 nm. Excess heparin (1:2, -□-, or 1:4, -▲-) disrupts this interaction, and the spectra resembles that of a protein in a random coil conformation. Spectra are heparin and/or blank (water) corrected.

FIG. 4 CD spectroscopy of $(AKKARA)_2$(SEQ. ID. NO:14) in the presence or absence of low $M_r$ heparin. The CD spectra measurements of $(AKKARA)_2$ (SEQ. ID. NO:14) in the absence of heparin (1:0, -●-), indicates a charged coil conformation (peaks at 195 and 216 nm, crossover at 210 nm). However, in contrast to the heparin-induced conformational change seen for the high affinity heparin-binding peptide $(AKKARA)_6$ (SEQ. ID. NO:13), $(AKKARA)_2$ (SEQ. ID. NO:14), which binds heparin weakly, remains a charged coil in the presence of heparin (1:0.25, -○-; 1:0.50, -X-; 1:0.75, -■-; 1:1, -□-).

FIGS. 5A and 5B: ACE analysis of the interactions between peptides containing heparin-binding consensus sequences and HUVEC PGs. ACE gel images as obtained by a phosphorimager in which (FIG. 5A) EC PGs/GAGs or (FIG. 5B) heparin was fractionated through peptides. In FIG. 5A, at least two populations of high affinity PG/GAG, seen as two bands of radiolabeled material migrating with different mobilities, is visible at peptide concentrations of ≦50 nM. At a peptide concentration of 250 nM (near the Kd≅300 nM), a separation of the PG/GAG species is evident as a broad smear throughout the lane, and as a sharp band that migrates approximately half way down the lane, indicating heterogeneity in size, charge density and/or peptide binding interactions of the PG/GAG population. PG/GAG samples in which HSPGs have been chemically degraded by nitrous acid (EC PGs/NA), also displayed high binding affinity ($K_d \cong 300$ nM), implying that chondroitin/dermatan sulfates which remain in the sample bind the peptide strongly. In contrast to the heterogeneity seen in FIG. 5A, FIG. 5B shows that heparin migrates as a single broad band of radiolabeled material.

Figure 6:
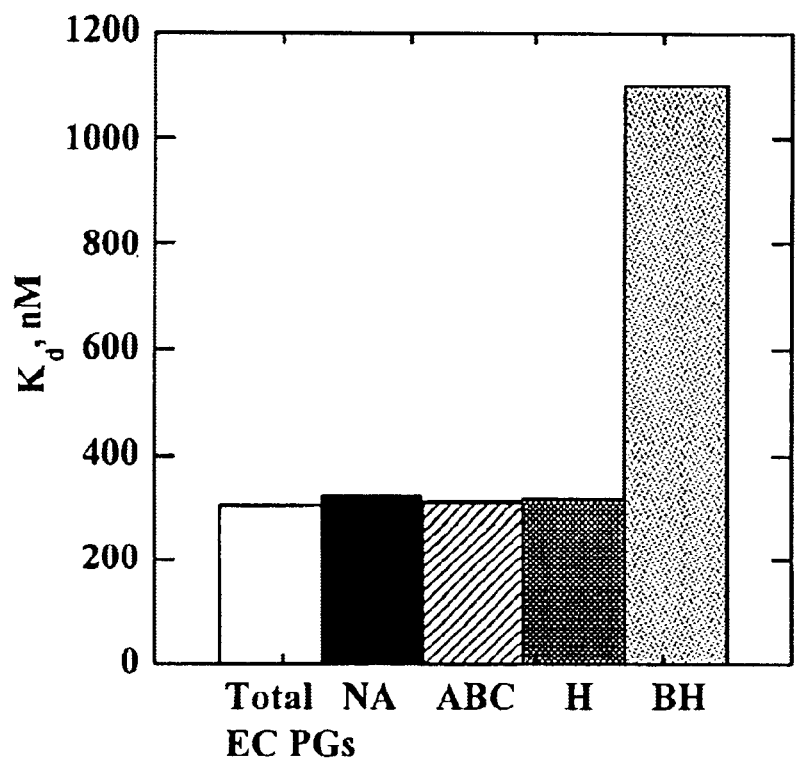

FIG. 6 Affinity of $(ARKKAAKA)_4$ (SEQ. ID. NO:8) for HUVEC PGs and PG components. The peptide was analyzed for binding affinity to HUVEC PGs/GAGs by ACE, and the $K_d$ of the peptide-PG/GAG interactions were calculated from binding plots as detailed in Experimental Procedures. Similar affinities (~300 nM) were obtained for total PGs, for PG samples devoid of HS GAGs via nitrous acid treatment (NA) or heparatinase I digestion (H), and for PGs devoid of CS GAGs via chondroitinase ABC (ABC) digestion. Liberation of GAG chains from the core protein by borohydride reduction (BH) of total PGs caused a 3-fold reduction in affinity ($K_d \cong 1200$ nM).

FIGS. 7A–7J: Neutralization of Lovenox by Peptides in Vivo: Anti-Factor Xa Assay. Neutralization of Lovenox by Peptides in Vivo: Anti-Factor Xa Assay Absorbance @ 405 nm defines the heparin concentration in the plasma as a function of the amount of anti-Factor Xa activity. Heparin complexes with Antithrombin III and the complex inhibits Factor Xa. The amount of Factor Xa activity is determined by the change in $A_{405}$ over 1 minute by chromogenic assay. The low point on each curve represents the highest amount of anti-Factor Xa activity, a function of the highest concentration of heparin obtained in the particular animal. $A_{405}$ of 1.0 represents about 0.5U/ml of anti-Factor Xa activity, and $A_{405}$ of 0.5 represents about 1.0 U/ml anti-Factor Xa activity, based on standardization against Hepanorm low molecular weight heparin standards for the Stachrom Heparin kit. Administration of the peptide results in formation of a peptide/heparin complex, thus reducing the amount of ATIII-heparin complex and therefore reducing Factor Xa activity, resulting in reduced breakdown of the dye and return to baseline of the $A_{405}$. Rats were injected with Lovenox alone (FIG. 7A) or with Lovenox followed by peptide three minutes after injection of Lovenox (arrow) (FIGS. 7B–7J). Peptides were administered at 2 mg/300 gm animal except where noted otherwise. Blood samples (0.1 ml) were obtained for anti-Factor Xa analysis immediately before the injection of Lovenox, at 30-second intervals after the injection until 10 minutes, then at 1 minute intervals until 15 minutes, and at 5-minute intervals until 30 minutes.

DETAILED DESCRIPTION

Peptides included in the present invention (all single letters represent conventional nomenclature designations for amino acids):
1. $(ARKKAAKA)_n$ (SEQ. ID. NO:5)
2. $(AKAAKKRA)_n$ (SEQ. ID. NO:15)
3. $(AKKARA)_n$ (SEQ. ID. NO:4)
4. $(ARAKKA)_n$ (SEQ. ID. NO:16)
5. YPARRARYQWVRCKP (SEQ. ID. NO:9)
6. YPTQRARYQWVRCNP (SEQ. ID. NO:10)

Examples of variations of the above peptide motifs included in this patent:
A. $(XBBBXXBX)_n$ or $(XBXXBBBX)_n$ where B denotes arginine (R), lysine (K) or a combination of the two, X denotes preferably but is not limited to alanine (A) or glycine (G), and n≧2. For example some possible permutations of the sequences covered by these patents will include but not be limited to:
$(ARRRAARA)_n$ (SEQ. ID. NO:17) $(ARRKAAKA)_n$ (SEQ. ID. NO:18)
$(AKKRAAKA)_n$ (SEQ. ID. NO:19) $(ARAARRRA)_n$ (SEQ. ID. NO:20)
$(ARAAKRKA)_n$ (SEQ. ID. NO:21)
$(GRRKGGRG)_n$ (SEQ. ID. NO:22) $(GRKKGGRG)_n$ (SEQ. ID. NO:23)
$(GKKKGGRG)_n$ (SEQ. ID. NO:24) $(GRGGKRRG)_n$ (SEQ. ID. NO:25)
$(GRGGKKRG)_n$ (SEQ. ID. NO:26)
B. $(XBBXBX)_n$ or $(XBXBBX)_n$ where B is arginine (R), lysine (K) or a combination of the two, X is preferably but not limited to alanine (A) or glycine (G), and n≧2. For example some possible permutations of the sequences covered by these patents will include but not be limited to:
$(ARRARA)_n$ (SEQ. ID. NO:27) $(ARKAKA)_n$ (SEQ. ID. NO:28)
$(ARARRA)_n$ (SEQ. ID. NO:29) $(ARAKKA)_n$ (SEQ. ID. NO:30)
$(GRRGKG)_n$ (SEQ. ID. NO:31) $(GKKGRG)_n$ (SEQ. ID. NO:32)
$(GRGRKG)_n$ (SEQ. ID. NO:33) $(GKGKRG)_n$ (SEQ. ID. NO:34)
C. Inclusion of a single cysteine (C) within 3 residues of either the N- or C-terminus as in YPARRARYQWVRCKP (SEQ. ID. NO:9), or YPTQRARYQWVRCNP (SEQ. ID. NO:10) or in peptide sequences $(XBBBXXBX)_n$, $(XBXXBBBX)_n$, $(XBBXBX)_n$, or $(XBXBBX)_n$, where n≧2. For example some possible permutations of the sequences covered by these patents will include but not be limited to:
ARRKAARA-ARRKACRA (SEQ. ID. NO:35)
ARCAKKRA-ARAAKKRA-ARAAKKRA (SEQ. ID. NO:36)
ARRAKA-ARRAKA-ARRCKA (SEQ. ID. NO:37)
AKCKRA-AKAKRA (SEQ. ID. NO:38)
D. For any of the above peptides, this patent will also cover inclusion of the D- isomer forms of amino acids in place of the L-forms, or inclusions of any combinations of D- or L-isomer forms to create reagents resistant to proteolytic degradation for in vitro and in vivo applications.
E. For any of the above peptides, this patent will also cover inclusion of any other amino acids in any X position.
F. This patent will also include peptides which incorporate multiple copies of the heparin-binding consensus sequences, but which are not necessarily arranged as concatamers, e.g., two such peptides may be ARKKAARAAAAAAAARKKAARA (SEQ. ID. NO:39) or ARKKAARAAAAAAAAAAAAAAARKKAARA (SEQ. ID. NO:40).

Embodiments of This Invention

The present invention relates to a number of different peptides of various sequences and sizes, including pharmaceuticals or bioactive agents composed of the peptides complexed with or incorporated into delivery vehicles such as salts, solutions, solvents, and/or carriers, and/or covalently linked to other bioactive agents. These approaches are well known in the art and thus will not be discussed in great detail here. For example, the peptides may be used as pharmaceutical salts of agents including, but not limited to alkali metal salts, organic carboxylic or sulfonic acids, or inorganic acids, etc. Acceptable carriers for the peptides may include any of a variety of diluents, solvents, time release polymers, fillers, or binders, etc, and formulated into dosage forms such as pills or injectable solutions, etc. This patent also includes any of the peptides derivatized with functional groups and/or linked to other molecules to facilitate their delivery to specific sites of action, to potentiate their activity, or complexed covalently or non-covalently to other pharmaceuticals, bioactive agents, or other molecules. Such derivatizations must be accomplished so as to not significantly interfere with the heparin- or PG-interactive properties of the peptides. Carriers and derivatizations must also be designed or chosen so as not to exert toxic or untoward activities on animals or humans treated with these formulations. Functional groups which may be covalently linked to the peptides may include, but not be limited to, amines, alcohols, or ethers. Functional groups to be covalently linked to the peptides to increase their in vivo half lives may include, but not be limited to, polyethylene glycols, small carbohydrates such as sucrose, or peptides and proteins. The peptides may also be synthesized by recombinant DNA techniques with expression vectors for use in biological systems, such as bacteria, yeast, insect, or mammalian cells. Methods are well known in the art.

Design and Synthesis of Novel High Affinity Heparin-Binding Peptides and Determination of Their Heparin- and EC PG-Binding Affinities.

Peptide Synthesis—Peptides were synthesized and purified by the University of Virginia Biomolecular Research Facility (Charlottesville, Va.) or by Genosys Biotechnologies (The Woodlands, Tex.). Peptides were synthesized by standard solid phase synthesis using FMOC chemistry. Peptide molecular weight was verified by mass spectroscopy, and purity (>70%) analyzed by HPLC.

Preparation of Radiolabeled Heparin—Whole heparin from pig intestinal mucosa (Sigma) was tyramine end-labeled and radiolabeled with $Na^{125}I$ (Amersham, Pharmacia Biotech, Inc., Piscataway, N.J.) to an average specific activity $\cong 1.0 \times 10^7$ CPM/μg as described[59]. Radiolabeled heparin was fractionated on Sephadex G-100 (Bio-Rad Laboratories, Hercules, Calif.) and the final $\cong 12\%$ of material to elute was retained as the low $M_r$ material of $\leq 6,000$ (Jordan, R., D. Beeler, and R. Rosenberg, *J Biol Chem*, 254:2902–2913, 1979; Laurent, T. C., et al., *Biochem J*, 175:691–701, 1978).

Electrophoretic Analysis of Binding of Heparin and Human Umbilical Vein Endothelial Cell (HUVEC) PGs to Peptides—Binding of radiolabeled heparin and HUVEC PGs to peptides was studied by ACE as detailed elsewhere (McPherson, J. M., et al., *Collagen Ref Res*, 1:65–82, 1988), since the heparin-protein binding affinities revealed by ACE match reasonably well with those obtained by other well established quantitative techniques for measuring binding interactions, e.g., (McPherson, J. M., et al., *Collagen Rel Res*, 1:65–82, 1988; San Antonio, J. D., et al., *J Cell Biol*, 125:1179–1188, 1994; San Antonio, J. D., et al., *Glycobiol*, 4:327–332, 1994; Tsilibary, E. C., et al., *J Biol Chem*, 263:19112–19118, 1988). Briefly, peptides were dissolved in 1×ACE running buffer, 50 mM sodium 3-(N-morpholino)-2-hydroxypropanesulfonate (MOPSO, Sigma)/ 125 mM sodium acetate, pH 7.0, and serially diluted in running buffer at 2× concentrations. Peptides were then mixed 1:1 with 2% agarose/1% CHAPS, 3-[(3-cholamidopropyl)dimethylammonio]-1-propanesulfonate, (Boehringer Mannheim, Indianapolis, Ind.), and loaded into wells of a 1% agarose gel. Radiolabeled heparin or HUVEC PGs were then loaded in a slot on the anode side of the gel, and electrophoresed through the peptide-containing wells, towards the cathode. Gels were dried and PG mobility was measured with a Phosphorimager (Molecular Dynamics, Sunnyvale, Calif.) by scanning each protein lane and determining the relative radioactivity content per. 88-μm pixel through the length of the lane. Retardation coefficient (R) measurements, binding isotherm curve fittings, and apparent $K_d$ value determinations were calculated as detailed previously (Lee, M. K., and A. D. Lander, *Proc Nat Acad Sci USA*, 88:2768–2772, 1991; San Antonio, J. D., et al, Biochem, 32:47464755, 1993).

Some peptides were also analyzed by ACE for heparin-binding under reducing conditions. Thus, after serial peptide dilution, β-mercaptoethanol (β-ME) was added at 5% to each peptide sample, and these were mixed 1:1 with 2% agarose/1% CHAPS/5% β-ME, and added to the ACE gel sample wells as usual.

Binding analysis of peptides to enzymatically or chemically degraded PGs (see below) was carried out by ACE as detailed, except that PG samples included 6 M urea to denature any residual enzymes.

Cell Culture—HUVEC were isolated as detailed elsewhere (Gimbrone, M. A., In Progress in Hematology and Thrombosis. Vol. III. B. S. Collen, editor. W B Saunders, Philadelphia. 1–28, 1976) and were used up to passage seven. Cells were cultured on 0.2% gelatin-coated tissue culture flasks in normal culture media composed of medium 199 (Gibco BRL, Gaithersburg, Md.), 10% fetal bovine serum (FBS, Mediatech Inc.), 80 μg/ml endothelial cell growth supplement isolated from bovine hypothalami as described (Maciag, T., et al., *Proc Nat Acad Sci USA*, 76 (11):5674–5678, 1979), 50 μg/ml heparin (porcine intestinal mucosa, grade 1A, Sigma) 1% penicillin-streptomycin, and 0.1% fungizone.

Radiolabeling and Isolation of Total HUVEC PGs and GAGs—Exponentially growing, subconfluent HUVEC were labeled with 35μCi/ml $^{35}S-Na_2SO_4$ (ICN Pharmaceuticals, Costa Mesa, Calif.) in normal culture media minus heparin for 12 h. Culture media and cell layers were harvested separately. After removal of the media, cells were washed with 2.0 ml PBS plus $Ca^{2+}$-$Mg^{2+}$. Media and rinses were pooled and brought to 6 M urea, 10 mM EDTA, 1 mM phenymethylsulfonyl fluoride (PMSF), 5 mM N-ethylmaleimide (NEM), 50 mM 6-aminocaproic acid, 5 mM benzamidine, and 1 μg/ml pepstatin A. Samples were stirred for 15 min at room temperature, then centrifuged at 10,000 rpm for 30 min to remove insoluble materials.

To the cell layer was added 2.0 ml of extraction solution, 6M urea, 100 mM NaCl, 0.2% Triton X-100, 50 mM Tris-HCl, pH 7.0, and protease inhibitors as described above. Cells were scraped off the dishes, and the extracts were pooled and stirred for 5 min at room temperature, and then centrifuged as described above.

Samples were concentrated on DEAE columns (DEAE Bio-Gel A Agarose, Bio-Rad Laboratories) equilibrated with low salt buffer, 0.1 M NaCl, 6 M urea, and 50 mM Tris-HCl, pH 7.0. Columns were rinsed with 10 ml of low salt buffer; flow through was discarded. Bound PGs/GAGs were eluted with 3 ml of high salt buffer, 1.5 M NaCl, 6 M urea, and 50 mM Tris-HCl, pH 7.0. Eluted samples were dialyzed against distilled water, lyophilized and stored at −20° C. until binding analysis.

Enzymatic Digestions of PGs—The contributions of PG GAG chain components to peptide binding affinities were assessed by selective enzymatic degradation of GAG chains prior to ACE analysis. $^{35}$S-Na2SO$_4$ labeled HUVEC PGs were digested with chondroitinase ABC, or heparatinase I (Seikagaku America, Ijamsville, Md.). PG samples were resuspended in 100 μl enzyme buffer [chondroitinase buffer: 50 mM Tris-HCl, 30 mM sodium acetate, pH 8.0, 0.1 mM pepstatin A, 0.5 mg/ml BSA, 10 mM NEM, 1 mM PMSF, and 5 mM EDTA; heparatinase buffer: 50 mM Tris-HCl, 5 mM calcium acetate, pH 7.0, 0.5 mg/ml BSA, and 1 mM PMSF]. Samples were digested with 0.05 U/ml chondroitinase ABC at 37° C. for 3 h. Fresh enzyme was then added to the same concentration and the incubation continued for an additional 1 h. Heparatinase I was added to samples at 0.01 U/ml. Samples were incubated for 3 h at 43° C., and fresh enzyme was then added to the same concentration, and incubation continued for an additional 1 h. All samples were then stored at −20° C. until binding analysis.

Chemical Degradation of PGs—The contributions of PG GAG chain components to peptide binding affinities were further assessed by selective chemical degradation. Total secreted HUVEC PGs were subjected to nitrous acid degradation as detailed (Shively, J. E., and H. E. Conrad, Biochem, 15:3932–3942, 1976), which selectively degrades HS GAG chains. Binding analysis to peptides was then measured by ACE.

β-elimination of PGs—GAG chains were released from PG core proteins by alkaline borohydride reduction as detailed (Iozzo, R. V., and W. Muller-Glauser, Canc Res 45:5677–5687, 1985).

Circular dichroism spectroscopy—Circular dichroism (CD) spectra were recorded at 22° C. using a JASCO J-500 C spectropolarimeter interfaced to a 486 PC. The path length of the CD cells was 0.5 mm, and the CD was expressed in terms of ellipticity [Θ] in degreee●cm$^2$●dmol$^{-1}$. Samples were initially dialyzed to water to remove residual synthesis contaminants, lyophilized, and resuspended in water at 1 mg/ml and the pH was adjusted to 7.0. Peptide concentrations of 0.1 mg/ml or 0.2 mg/ml were analyzed. Typically, two scans were averaged for each spectrum. CD spectra of peptides in α-helical conformations were recorded in the presence of trifluoroethanol (TFE), which served as a positive control of peptides in α-helical conformations. To determine the effects of heparin on peptide conformation, solutions containing peptide plus heparin were prepared at various peptide: heparin ratios (wiw).

Analysis of Peptide Concentration—Concentrations of peptides used in CD were verified by ID NMR spectroscopy based on an internal 2,2-dimethylsilapentane-5-sulphonate (dss) standard. NMR experiments were recorded on a Bruker AMX 600 NMR spectrometer equipped with a 5 mm broadband inverse probe, using the XwinNMR 2.1 software package run on a Silicon Graphics INDY work station. ID proton spectra were acquired at 303K using a 4 s relaxation delay and were processed with 0.5 Hz exponential line broadening. 250 pil of a 1 mg/ml peptide solution (as determined by weight) was lyophilized and dissolved in 405 μl D20, containing 0.123 mM DSS. The degenerate arginine δCH$_2$ resonances at 3.2 ppm, ascertained by a TOCSY experiment, were integrated and compared to the internal standard.

Results:

Peptide-heparin interactions—To design small peptides which exhibit high affinities for heparin and for the GAG components of PGs, peptide sequences were modeled after proposed heparin-binding consensus sequence motifs. Thus, a collection of peptides containing one of two consensus sequence motifs, either XBBXBX or XBBBXXBX, as well as various modifications of these, were synthesized (Table I). As peptides containing a single heparin-binding sequence often show little or no affinity for heparin (Conrad, H. E., Heparin-Binding Proteins. Academic Press, San Diego, 1998), a strategy used here was to include consensus sequences in multiple copies within peptides. In initial studies we selected for synthesis the sequences (AKKARA), (SEQ. ID. NO:4) or (ARKKAAKA)$_n$ (SEQ. ID. NO:5), where n=1–6. Alanine was included in the hydropathic positions because of its stabilizing activity on α-helices (Ferran, D. S., et al., Biochem, 31:5010–5016, 1992) and the basic amino acids were chosen to represent those with the highest probability of occurrence in each basic position in the heparin-binding consensus sequences of native heparin-binding proteins (Cardin, A. D. and H. J. R. Weintraub, Arteriosclerosis, 9:21–32, 1989). When single copies of either sequence were tested for heparin-binding by ACE, no affinities were detected. In contrast, peptides containing two copies of the consensus sequence exhibited weak but detectable affinities for heparin (<6 μM), and peptides of higher molecular weight containing 4-6 copies of a consensus sequence showed a marked increase in heparin-binding affinity (40–150 nM) (FIG. 1). The heparin-binding affinity of both the 6-mer and 8-mer tandem-repeat peptides reached a plateau as peptide length approached 30 amino acids [(AKKARA)$_5$ (SEQ. ID. NO:41), K$_d$≅90 nM and (ARKKAAKA)$_4$ (SEQ. D. NO:8), K$_d$≅40 nM]. Larger peptides [(AKKARA)$_6$ (SEQ. ID. NO:13) and (ARKKAAKA)$_5$ (SEQ. ID. NO:42)] displayed similar affinities (K$_d$≅100 and 50 nM respectively, Table I).

To define the sequence and conformational features of the tandem-repeat peptides which confer their high affinity heparin-binding characteristics, peptides containing variants of one of the consensus sequences first tested, (ARKKAAKA)$_3$ (SEQ. ID. NO:43), were synthesized. These included those in which alanines were replaced by other hydropathic residues, the spacings between consensus sequences were altered by removal or addition of alanine residues, or the potential of the peptides to form stable α-helices was inhibited by including proline residues at various positions. It was found that peptide affinity for heparin was decreased when alanine was replaced by glycine in all the hydropathic positions [(ARKKAAKA)$_3$ (SEQ. ID. NO:43) K$_d$≅135 nM, (GRKKGGKG)$_3$ (SEQ. ID. NO:44) K$_d$≅200 nM, p<0.01]; less conservative substitutions had varying effects on heparin-binding affinity, i.e. for (LRKKLGKR)$_3$ (SEQ. ID. NO:45), K$_d$≅105 nM, affinity was unaffected; for (TRKKLGKI)$_3$ (SEQ. ID. NO:46), K$_d$≅740 nM, (p<0.01) affinity was decreased (Table I).

Two peptides were synthesized in which the spacings between adjacent consensus sequences were altered. Both increasing (ARKKAAKA-AAAA-ARKKAAKA-AAAA-ARKKAAKA, SEQ. ID. NO:47) or decreasing (ARKKAAKA-RKKAAKA-RKKAAKA, SEQ. ID. NO:48) the distance between consensus sequences resulted in decreased heparin-binding affinity (K$_d$≅250 and 450 nM respectively). Inclusion of prolines also decreased the heparin-binding affinity, the degree of which was influenced by their position and number. Thus, the heparin-binding affinity decreased to 360 nM when prolines were present in each tandem repeat in place of an alanine: (ARKKPAKA)$_3$ (SEQ. ID. NO:49); however, a weaker affinity was obtained when a single proline was substituted in the center of a series of three heparin-binding consensus sequences (ARKKAAKA-ARKKPAKA-ARKKAAKA (SEQ. ID. NO:50), K$_d$ ≅730 nM, Table I).

Figure 2:
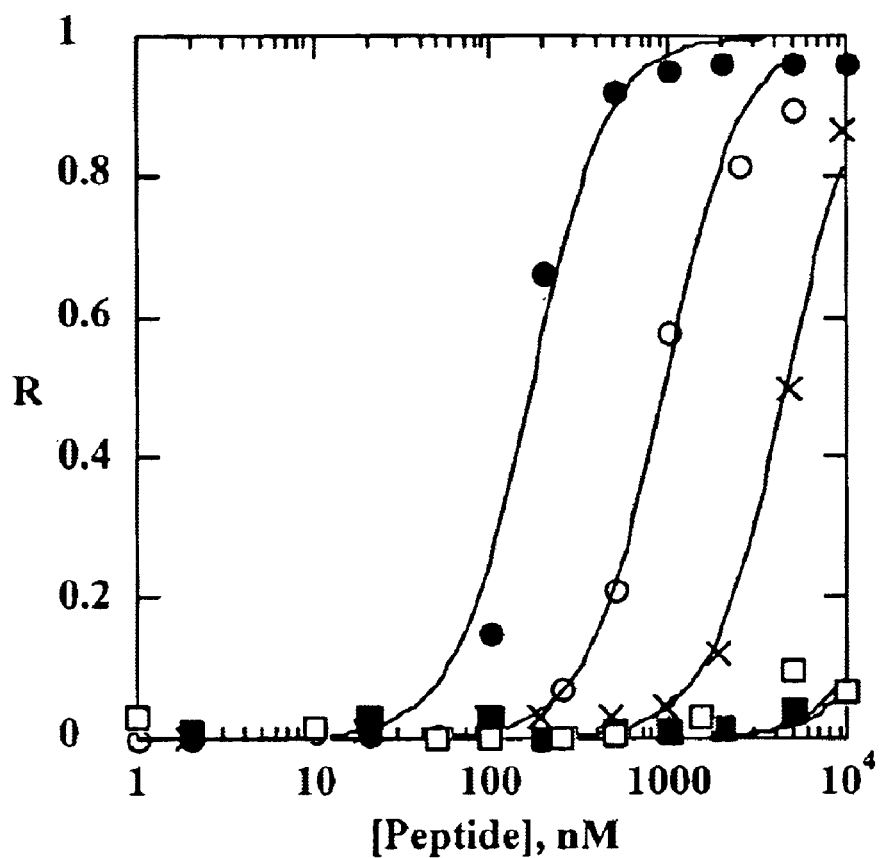

Other peptides synthesized and studied include sequences native to the mouse (YPARRARYQWVRCKP, SEQ. ID. NO:9) or human (YPTQRARYQWVRCNP, SEQ. ID. NO:10) serglycin (SG) core proteins, which contain either a single or partial consensus sequence, respectively. These showed significant affinities for heparin ($K_d \approx 200–900$ nM, Table I and FIG. 2), despite their small sizes (about 2000 Da). To elucidate the basis for the strong heparin-binding features of these peptides, the ability of the basic residues to sustain high affinity binding was tested by studying a peptide which contained all the basic residues of the mouse sequence in their native positions, but in which all other residues were changed to alanines (AAARRARAAAARAKA, SEQ. ID. NO:11). A 350-fold decrease in heparin-binding affinity ($K_d \approx 72$ μM) for this peptide indicated that the number and arrangement of basic residues in the mouse sequence was not sufficient for high affinity binding, and suggests the importance of one or more of the other non-basic residues (FIG. 2). We next tested whether the C-terminal cysteine in the mouse SG peptide may promote peptide dimer formation, thereby influencing heparin-binding affinity. Thus, heparin-binding was tested by ACE under reducing conditions, and it was found that this treatment yielded negligible heparin-binding. Likewise, when the cysteine residue was replaced by an alanine in the native mouse SG sequence, (YPARRARYQWVRAKP, SEQ. ID. NO:12), heparin-binding affinity was again negligible; both results are consistent with the potential cross-linking function of the cysteine residues (FIG. 2).

Figure 3:
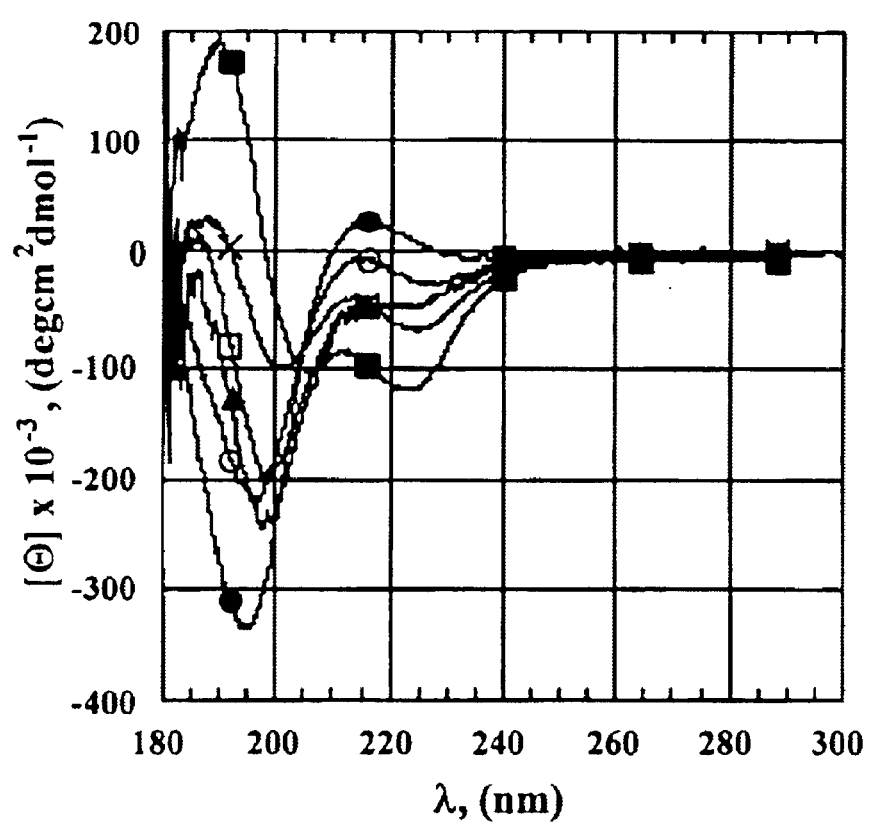

The intrinsic structural properties of the peptides were explored using CD spectroscopy. Short peptides of known heparin-binding proteins containing heparin-binding consensus sequences have previously been shown to fold into aαhelical conformations. In doing so, the basic amino acids locate to one face of the helix, and thus are potentially exposed for binding. Peptides which displayed weak (AKKARA)$_2$ (SEQ. ID. NO:14), moderate (AKKARA)$_4$ (SEQ. ID. NO:51), and strong (AKKARA)$_5$ (SEQ. ID. NO:41) and (AKKARA)$_6$ (SEQ. ID. NO:13), heparin-binding affinities, were analyzed by CD to characterize their degree of α-helical contents and propensities to form an α-helix. All peptides exhibit very similar spectra with peaks at 195 nm and 216 nm and a crossover at 210 nm [for example, see FIG. 3, (AKKARA)$_6$ (SEQ. ID. NO:13), 1:0, -●-, and FIG. 4 (AKKARA)$_2$ (SEQ. ID. NO:14), 1:0, -●-]. These spectra are indicative of an extended charged coil conformation that was previously reported for charged poly (L)-lysines and poly(L)-arginines (Gelman, R. A., et al., *Biopolymers*, 12:541–558, 1973):

Intrinsic CD of the peptides shows that they do not adopt α-helical conformations. To explore the conformational repertoire of the peptides and to record CD spectra for the α-helical conformations, peptides were analyzed by CD in the presence of the non-polar solvent TFE. Non-polar solvents are known to increase the degree of α-helicity of a peptide in solution by enhancing hydrogen bonding and electrostatic interactions (Adler, A. J., and G. D. Fasman, *J Phys Chem*, 75:1516–1526, 1971). CD of (AKKARA)$_6$ (SEQ. ID. NO:13), at 0.1 mg/ml containing 0, 10, 20, 30, 40, and 50% TFE (v/v) was measured. At TFE concentrations >30%, with an apparent maximal effect induced at 40% TFE, the peptide assumes an α-helical conformation with classic α-helical peaks at 206 and 220 nm and a cross over at 197 nm (data not shown).

The CD spectra of (AKKARA)$_6$ (SEQ. ID. NO:13) recorded in the presence of increasing amounts of heparin (FIG. 3) demonstrates that a change from a charged coil conformation displayed in the absence of heparin (1:0) occurs upon heparin addition (1:0.25, 1:0.50, 1:1). Heparin induces a similar α-helical conformation at a 1:1 peptide: heparin ratio that was obtained in the presence of >30% TFE, with classic α-helical peaks at 190, 207, and 222 nm. At higher heparin concentrations (1:2 or 1:4) the α-helical form is lost and the spectrum resembles that of a random coil structure. This ability of excess GAG to disrupt the α-helical conformation of a polypeptide in solution has been reported previously (Gelman, R. A., et al., *Biopolymers*, 12:541–558, 1973).

Figure 4:
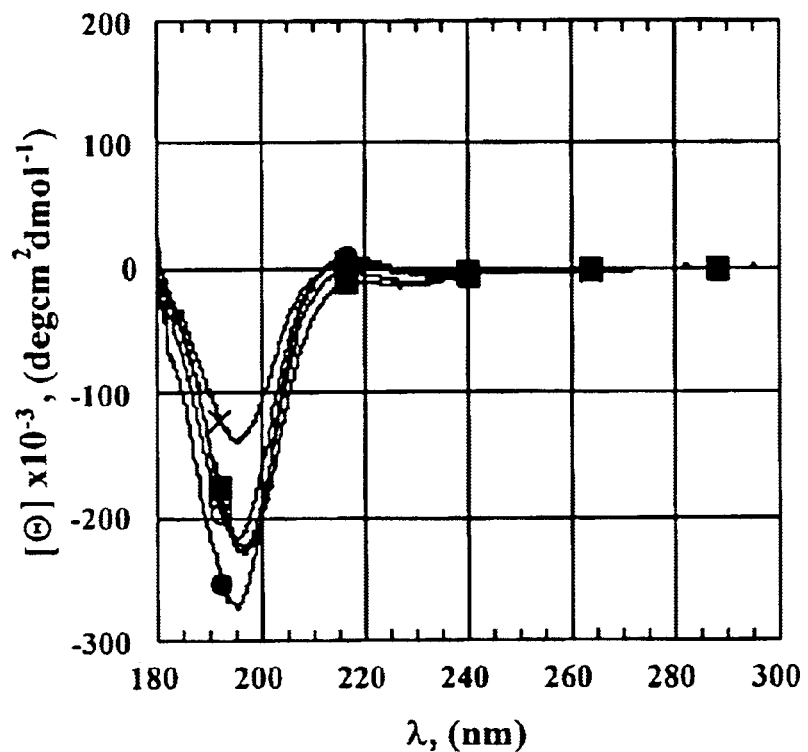

This same heparin effect is not obtained for the weak heparin-binding peptide (AKKARA)$_2$ (SEQ. ID. NO:14) (FIG. 4). In the absence of heparin (1:0), the peptide assumes a similar charged coil conformation as that observed for (AKKARA)$_6$ (SEQ. ID. NO:13), but fails to display α-helical character in the presence of heparin (1:0.25, 1:0.50, 1:0.075, or 1:1).

Peptide-PG interactions—The interactions between consensus sequence peptides and PGs were also examined. For these experiments total PGs were isolated from HUVEC cultures, since HUVEC have been shown to express a variety of types of HS and CS PGs, including, for example, syndecans, perlecan, glypican and biglycan (Mertens, G., et al., *J Bio Chem*, 267 (28):20435–20443, 1992; Jarvelainen, H. T., et al., *J Biol Chem*, 266 (34):23274–23281, 1991). Thus, cell layer-associated and secreted $^{35}$S—SO$_4$-radiolabeled PGs were purified by extraction with urea, and those PGs retained on DEAE after a 0.1 M NaCl rinse were studied for their binding to (ARKKAAKA)$_4$ (SEQ. ID. NO:8) by ACE (FIG. 5A, EC PGs). This peptide exhibited significant affinity for secreted HUVEC PGs, although the average affinity was somewhat weaker than that exhibited by the peptide for heparin (PG $K_d \approx 300$ nM, heparin $K_d \approx 50$ nM). Similar affinities were obtained for cell layer associated PGs (data not shown). Inspection of ACE gels in which secreted PGs were fractionated through peptides demonstrated the presence of at least two populations of PG evident as two distinct bands of radiolabeled material migrating through the peptide lanes with different mobilities (FIG. 5A, EC PGs). This difference in migration rate could indicate heterogeneity of the PG in size or charge. In contrast to the heterogeneity seen in FIG. 5A, FIG. 5B shows that heparin migrates as a single band of radiolabeled material Thus, to ascertain which GAG chains, as well as which PG component, (i.e. core protein, GAG chains, or both), were responsible for peptide-binding, total HUVEC PGs were subjected to various chemical and enzymatic degradations. Samples were then tested for their ability to bind to (ARKKAAKA)$_4$. (SEQ. ID. NO:8) PGs in which HS GAGs were chemically degraded by nitrous acid or enzymatically degraded by heparatinase I, were able to maintain comparable affinity for the peptide as was displayed by the total PG sample (FIG. 5A, EC PGs/NA and FIG. 6). PGs in which CS GAG chains were digested with chondroitinase ABC were also able to maintain comparable affinity for the peptide. Release of GAG chains from cores by borohydride reduction resulted in a 3–4 fold diminished affinity (FIG. 6).

Heparin Interactions with Commercial Polycations

For the binding of polylysines (purchased from Sigma Chemicals) to heparin, it was shown that at least for those polymers of high $M_r$ ($\approx 100$ kilodaltons), inclusion of either L- or D-amino acid isomer forms or combinations of these isomers in the polymers did not influence binding affinity. These data suggest that that inclusion of the D-isomer amino acid forms in the peptides described in this patent application will be useful in increasing their longevities for various applications (e.g., in vivo use or uses in vitro with living cells or cell or tissue extracts) where proteolytic processing of the peptides could present a problem.

Summary and Discussion:

The goal of these experiments was to design high affinity heparin- and PG-binding peptides; the strategy we used is to incorporate into their structure copies of sequences proposed to bind heparin in native proteins. Our approach is also based on the fact that truncation of peptide structure without loss of activity can sometimes be achieved by constraining or manipulating peptide conformation (Starovasnik, M. A., et al., *Proc Natl Acad Sci USA,* 94:10080–10085, 1997). In the case of apolioprotein E and apolipoprotein B-100, heparin-binding sites are believed to form α-helices upon heparin-binding, and molecular modeling illustrates that basic amino acids in the binding sites align to one side of the helix to form a region of high positive charge through which heparin-binding occurs (Cardin, A. D. and H. J. R. Weintraub, *Arteriosclerosis,* 9:21–32, 1989). Thus, in our design of heparin-binding peptides, we also incorporated structural features conducive to stable x-helicity.

In our initial experiments, families of peptides were synthesized that contained single or multiple copies of heparin-binding consensus sequences. When their heparin-binding was examined by ACE, peptides containing single sequences showed no measurable affinity for heparin. This result is as expected since peptides carrying single heparin-binding sequences found in native proteins often fail to display significant heparin-binding (Conrad, H. E., Heparin-Binding Proteins. Academic Press, San Diego, 1998), but they may contain multiple consensus sequences that come into proximity upon protein folding or multimerization, thereby enhancing heparin-binding through cooperativity (Huntington, J. A., et al., *Biochem,* 35:8495–8503, 1996). In contrast, the affinity of peptides (AKKARA)$_n$ (SEQ. ID. NO:4) or (ARKKAAKA)$_n$ (SEQ. ID. NO:5) ranged from weak ($K_d \cong 640$ μM) when n=2, to strong ($K_d \cong 50$–100 nM) when n=3–6. These latter affinities are in the range of those displayed by heparin-binding proteins such as bFGF ($K_d \cong 10$ nM), or type I collagen, ($K_d \cong 100$–200 nM) (San Antonio, J. D., et al., *Biochem,* 32:4746–47, 1993). However, the fact that the peptides are roughly 4 times smaller than bFGF and 100 times smaller than type I collagen highlights their significant heparin-binding abilities. The affinity appeared to plateau at n≧5, or 36–40 amino acids, suggesting that peptides of approximately 30–32 amino acids were of sufficient length to occupy all available binding sites on low $M_r$ heparin, and that additional amino acid residues beyond this did not contribute to heparin binding due to a lack of available ligand. However, this hypothesis can not be tested without knowing the M, distribution of the heparin used in these experiments.

Other experiments examined heparin binding by peptides including sequences native to proteins which contain a single or partial heparin-binding consensus sequence. Results again suggested the critical nature of peptide $M_r$ and number of consensus sequences to heparin-binding. Thus, surprisingly, a strong heparin-binding affinity was displayed by a peptide corresponding to the mouse SG proteoglycan core protein containing a single consensus sequence, YPAR-RARYQWVRCKP (SEQ. ID. NO:9) ($K_d \cong 200$ nM). However, the affinity was diminished over 200-fold by disulfide reduction, or replacement of the cysteine with alanine, thus implying that its strong heparin-binding relies on peptide dimerization, and that the other residues flanking the consensus sequence were of little consequence. Indeed, others have shown that inclusion of cysteines near peptide termini to promote disulfide bond formation may improve peptide-ligand binding (Starovasnik, M. A., et al., *Proc Natl Acad Sci USA,* 94:10080–10085, 1997); our results suggest this to be a simple strategy to greatly enhance the affinity of peptides for heparin. SG, cerebroglycan (with PRRLRL, SEQ. ID. NO:52) (Stipp, C. S., et al., *J Cell Biol,* 124:149–160, 1994), and perlecan (with TRRFRD, SEQ. ID. NO:53) (Murdoch, A. D., et al., *J Biol Chem,* 267 (12):8544–8557, 1992) are among the few PGs that contain heparin-binding consensus sequences on their core proteins. Interestingly, the SG core protein, which carries many heparin chains, migrates at twice its predicted molecular weight on PAGE gels under reducing conditions (Perin, J.-P., et al., *Biochem J,* 255:1007–1013, 1988); suggesting dimerization. This could result from GAG chains of one PG binding to the core protein of another, or core-core associations through disulfide bonding. The potential physiological function of such PG—PG interactions remains to be explored.

Additional consensus sequence peptides were designed to determine other aspects of peptide structure important to heparin-binding. Including glycine in place of alanine in the hydropathic positions weakened heparin-binding, and peptides in which arginine was included in all basic positions displayed higher affinity for heparin than did those containing arginines and lysines. The latter is consistent with work showing a higher affinity interaction of arginine-heparin and arginine-HS than lysine-heparin or lysine-HS (Fromm, J. R., et al., *Arch Biochem Biophys,* 232 (2):279–287, 1995). This suggests that the heparin-binding characteristics of the peptides developed here may rely on amino acid type and arrangement in addition to ionic interactions. Inclusion of prolines within or between consensus sequence motifs weakened affinity for heparin, possibly as a result of alterations in peptide secondary conformation; this issue was investigated in our CD experiments. Finally, changing the spacing between consensus motifs weakened affinity for heparin; however, sequence orientation did not appear to influence binding ability as long as the motifs were contiguous and in one orientation.

Molecular modeling of consensus sequences in native heparin-binding proteins predicts their presence within α-helical regions (Cardin, A. D. and H. J. R. Weintraub, *Arteriosclerosis,* 9:21–32, 1989). Additionally, GAG-directed conformational changes on polypeptides such as poly(L)-lysine and poly(L)-arginine have been identified (Gelman, R. A., et al., *Biopolymers,* 12:541–558, 1973; Gelman, R. A., and J. Blackwell, *Arch Biochem Biophys,* 159:427–433, 1973; Gelman, R. A., and J. Blackwell, *Biopolymers,* 13:139–156, 1974). Aqueous solutions of these polypeptides at neutral pH were shown by CD to adopt charged coil conformations, and to display α-helical conformations in the presence of heparin. Our results showed that peptides of the type (AKKARA)$_n$ (SEQ. ID. NO:4) have charged coil conformations at neutral pH. In the presence of heparin, however, a peptide that showed high affinity for heparin, (AKKARA)$_6$ (SEQ. ID. NO:13), underwent a conformational change to an α-helix. In the presence of excess heparin, a further conformational change produced a random coil structure. In contrast, a peptide which displayed weak heparin-binding, (AKKARA)$_2$ (SEQ. ID. NO:14), failed to undergo any conformational change. Thus, the solution conformation of a peptide and its propensity to change conformation in the presence of heparin may be an indication of its ability to bind to heparin strongly. These data and those from experiments examining the effects of including prolines in peptides, which are known to disrupt the α-helical conformation, suggest that peptide secondary structure facilitates heparin-binding.

Here we also examined the interaction between the high affinity heparin-binding peptide (ARKKAAKA)$_4$ (SEQ. ID. NO:8) and EC PGs. Results showed that ECs secreted several types of PGs/GAGs which displayed significant affinities for (ARKKAAKA)$_4$ (SEQ. ID. NO:8) (K$_d$≅300 nM). ACE gel images revealed the resolution of multiple PG/GAG species after their migration through the peptide-containing lanes, suggesting heterogeneity in PG/GAG charge, size, and/or binding affinities. It was found that the CSPGs or HSPGs likely bind the peptide similarly, since affinity was maintained even after treatment of total PGs with nitrous acid, which selectively degrades HS GAGs, heparatinase I or chondroitinase ABC. The free GAG chains had 3–4 fold lower affinity than the intact PGs. Thus the core proteins of certain EC PGs either may contribute to binding directly, or act as a tether to bring multiple GAGs into proximity for cooperative binding. Similar observations have been made previously for cartilage PG-type II collagen interactions (Toole, B., *J Biol Chem* 251:895–897, 1976) and SG-type I collagen interactions (Schick, B. P., et al., *J Cell Physiol*, 172:87–93, 1997). Our results are inconsistent with carbohydrate sequence selectivity in the binding of these peptides with EC PGs, since similar affinities for these peptides were displayed by either total EC PGs or its CSPG fraction.

Of note is that the heparin-binding peptides designed here incorporate concatamers of heparin binding consensus sequences, which should rarely, if ever, appear in native proteins. Nonetheless, the proposed characteristics of heparin-binding motifs in proteins, as set forth by Cardin and Weintraub based on their theoretical analysis of putative heparin-binding domains of native proteins (Cardin, A. D. and H. J. R. Weintraub, *Arteriosclerosis*, 9:21–32, 1989), hold true with our model peptides. Thus, our data suggest that peptides containing the Cardin and Weintraub heparin-binding consensus sequences may show a selective advantage in heparin-binding over certain other sequences which do not fit their criteria.

In summary, optimally active heparin-binding peptides should include multiple sequences of the types: (XBBXBX)$_n$ and (XBBBXXBX)$_n$. Sequence number and peptide M, are the most critical features; peptides should be of at least approximately 30 residues, which could be decreased to 15 if cysteine is included near either terminus to promote dimerization. Peptides should contain contiguous sequence arrays, without intervening residues between sequences. Alanine, which stabilizes α-helical conformation, should occupy the hydropathic residue positions, and arginine the basic positions. The high affinity PG- or GAG-binding peptides developed here, or derivatives thereof, could prove useful as tools for the promotion of cell-substratum attachment of PG-expressing cells, in the targeting of drugs to PG-expressing cells and PG-rich extracellular matrices, or as antagonists of GAG-mediated actions, e.g., neutralization of the anticoagulant activity of heparin, as is presented in this patent application.

Effects of the Heparin- and PG-Binding Peptides on the Reversal of Heparin Inhibition of Thrombin Activity:

What follows is a description of the effectiveness of the peptide compositions for counteracting the effects of unfractionated heparin, Lovenox, and Organan on Factor Xa activity in vitro, and on Lovenox in vivo. Heparin is administered to patients either as unfractionated heparin or as heparin fragments. The fragments are prepared in several different ways, and result in a heterogeneous mixture that varies according to the methods of preparation. The low molecular weight heparins currently approved for clinical use, the standard dosage in anti-Xa units where known, and their molecular weight distributions are:

| | | |
|---|---|---|
| Lovenox: | <2000 daltons | ≦20% |
| (3000–6000 | 2000–8000 daltons | ≧68% |
| α-Xa IU) | >8000 daltons | ≦15% |
| Fragmin: | <3000 daltons | 3–15% |
| (5000 α-Xa IU) | 3000–8000 daltons | 65–78% |
| | >8000 | 14–26% |
| Logiparin | 600–20,000 daltons | |
| (Denmark) | >10,000 daltons | 30% |
| Orgaran | Heparan sulfate | 84% |
| (750 α-Xa IU) | Dermatan sulfate | 12% |
| | Chondroitin sulfate | 4% |
| | Mean chain length | |
| | 5500 daltons | |

Heparin inhibits the activity of thrombin and Factor Xa by binding to AT III and thus enhancing the ability of antithrombin III to bind to these enzymes. The higher-MW heparins presumably act as a bridge between ATIII and thrombin, and the binding of both proteins to the same molecule of heparin appears to be important for thrombin inhibition by ATIII. Thus the low molecular weight heparins do not affect thrombin activity, but still render ATIII capable of inhibiting Factor Xa activity. Wakefield et al in PN 5,919,761 tested their peptides against two preparations of LMWH, Logiparin and Lovenox, and got very different results with protamine; protamine produced 60% reversal of Logiparin but only 30% against Lovenox, and the other peptides tested with both heparins likewise were more effective against Logiparin. There are insufficient data to judge whether these differences are due to differences in the concentration of active heparin sequences in the preparations, or differences in the molecular weight distributions of the heparin chains, which could result in different rates of removal from the circulation and thus different levels of anticoagulation in the animals after the 30-minute waiting period. It is difficult to assess these data also because the actual levels of anti-Factor Xa activity and the amounts neutralized, i.e. the absolute amounts of anti-factor Xa activity at the time of injection of the peptide, and at the subsequent time points, as well as the loss of anti-factor Xa activity due to natural clearance of heparin in the dogs, are not given. In the Harris study, the dose of unfractionated heparin was only about 25% of the standard dose/kg in humans, and thus it is difficult to assess the efficacy of their peptides without knowing the parameters just stated for the Wakefield studies. Thus we cannot correlate our data with those of the previous patents.

Methods for in vitro Determinations of the Effects of Peptides on Reversal of Factor Xa Activity Solutions of Lovenox, Orgaran, or unfractionated heparin (Sigma) were prepared in 0.32% sodium citrate or in normal human plasma to contain 0.5 U/ml anti-FXa activity. Calibrations were made against the standards provided by the Stachrom Heparin (Diagnostica Stago) assay kit. The heparin/ATIII complex was allowed to form at 37° C. for 2 minutes, peptide was added, the mixture was incubated for an additional 1–5 minutes, and then Factor Xa was added, and finally the color reagent, for one minute, and the absorbance was read at 405 nm. The increase in absorbance from the heparinized control to the test sample was divided by the difference in A$_{405}$ between the heparinized control and the control without heparin to obtain the % reversal.

As shown in the Table II, several of the peptides which we tested were highly effective against heparin, low molecular weight heparin, and orgaran in vitro, and the activity was correlated with the binding affinity to the LMWH of ≦6000 daltons which had been used for the ACE binding studies described above (Table I). The exception was the human serglycin peptide, which was highly effective against UFH and Orgaran, but not against Lovenox.

In vitro Effect of the Peptides on Reversal of Inhibition of Thrombin Activity by Unfractionated Heparin Plasma was obtained from normal donors. Thrombin concentration (human alpha thrombin, Enzyme Research Laboratories, South Bend, Ind.) was standardized to produce a clotting time of 20–22 seconds. Heparin was added at 0.5 IU anti-thrombin activity/ml. The clotting time for heparin alone was approximately 3 minutes. To test the effects of the peptides in this system, one minute after addition of heparin to the plasma, the peptides were added in concentrations ranging from 1–200 µg/ml. After one minute, thrombin was added and the clotting time determined. The effects of the peptides were concentration dependent. The clotting time was restored to normal values in all samples at the dosages shown below in Table III. The ability of the peptides to neutralize heparin inhibition of thrombin clotting time was consistent with the binding affinities shown in Table I, and with the effectiveness against low molecular weight heparin anti-Factor Xa activity in Table II.

In Vivo Effects of Peptides in Reversing Effects of Lovenox on Factor Xa Activity Methods:

Rats (300–400 gm) were anesthetized with ketamine/acepromazine and were cannulated in the left jugular vein and right femoral vein. Blood samples were all 0.1 ml. Blood was drawn immediately before injection of Lovenox to establish baseline Factor Xa activity. Lovenox (43 IU anti-FXa activity/kg in 0.1 ml saline, based on suggested dosage for humans) was injected through the jugular catheter, followed immediately by 0.2 ml of saline. Blood (0.1 ml) was collected into sodium citrate from the femoral vein every 30 seconds for 3 min. The peptide was injected at 3 min through the jugular catheter in 0.1 ml of phosphate-buffered saline, followed by a 0.2 ml saline flush. Peptides were administered at 2 mg except where noted otherwise. Blood collection was immediately resumed every 30 seconds until 10 minutes after the initial Lovenox injection, then at 15, 20, 25 and 30 min. The samples were centrifuged to obtain plasma and were assayed for residual Lovenox by assay of anti-FXa activity by the Stachrom Heparin test kit. A405 was measured after a 1-minute incubation with the chromogenic Factor Xa substrate. The assay is described in further detail in the Figure Legend to FIGS. 7A–7J.

Results

The animals appeared to tolerate the administration of the heparin and the peptide without obvious changes in heart rate and respiration. No animals died following administration of the peptides of interest in this application, although one animal died following administration of Protamine. The results are shown in FIGS. 7A–J.

Figure 7A:
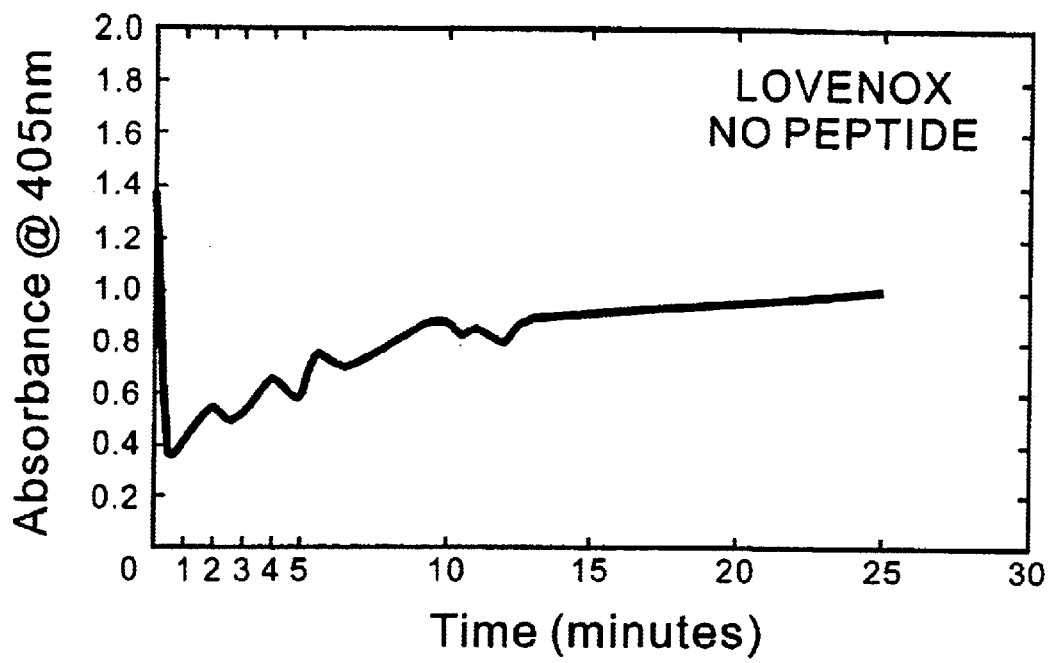
Figure 7B:
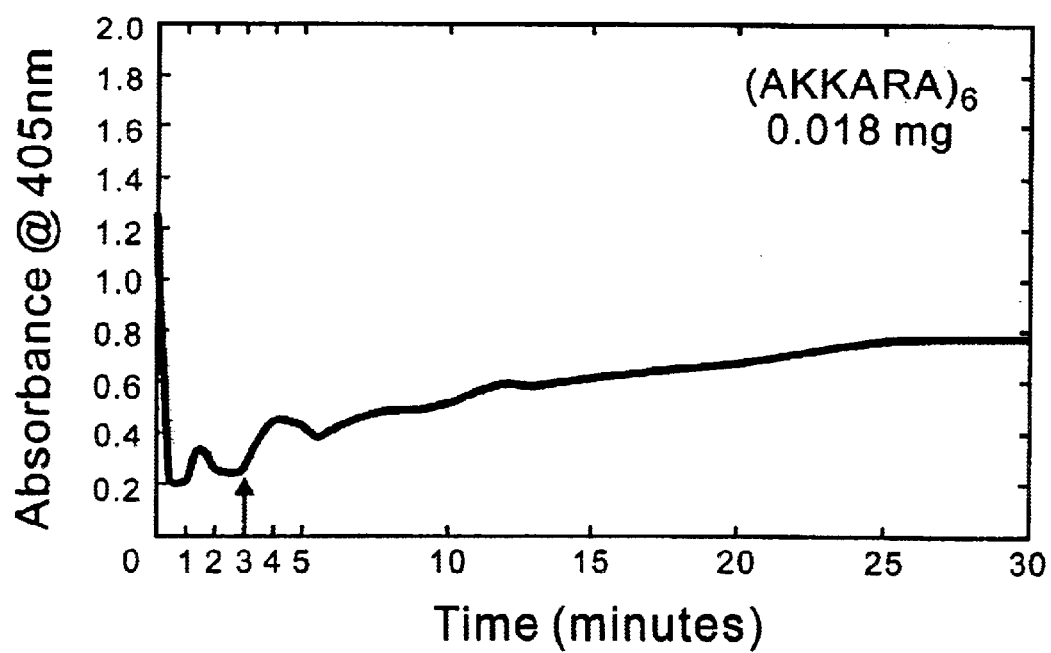
Figure 7C:
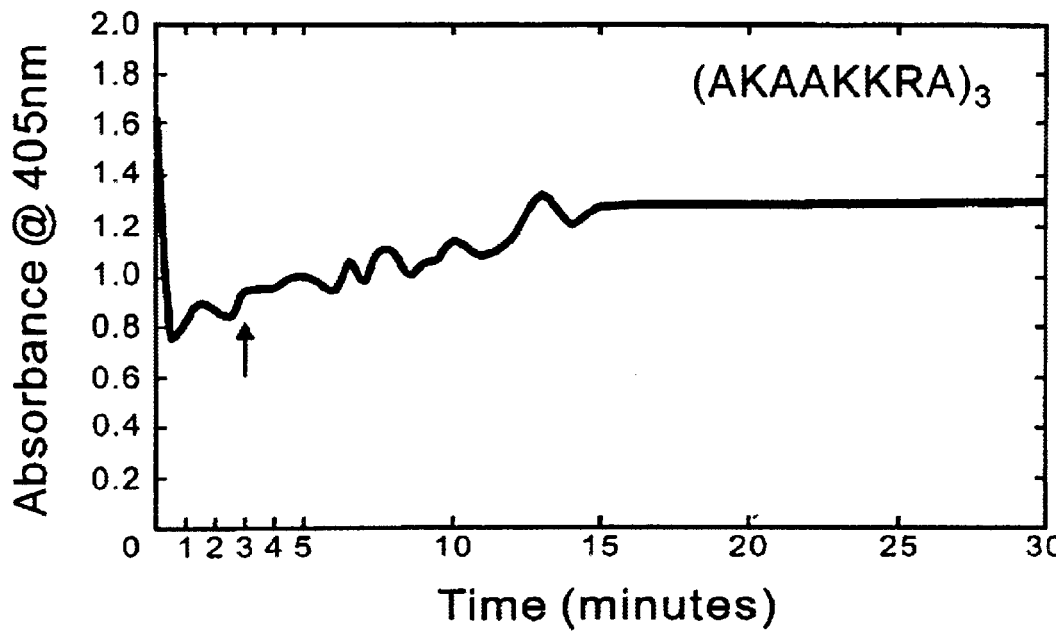
Figure 7D:
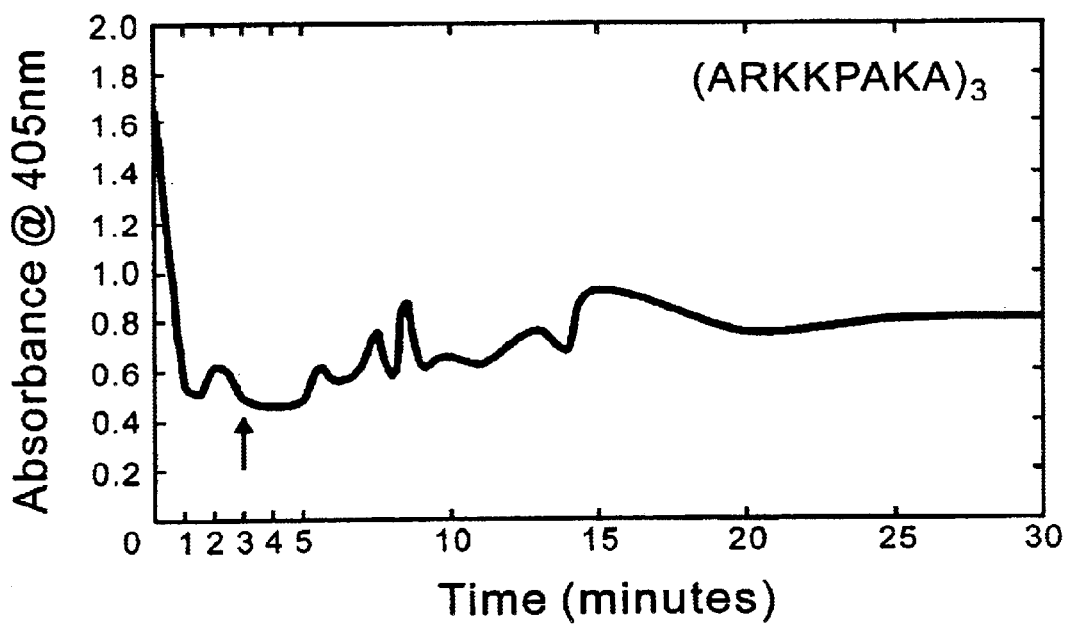
Figure 7E:
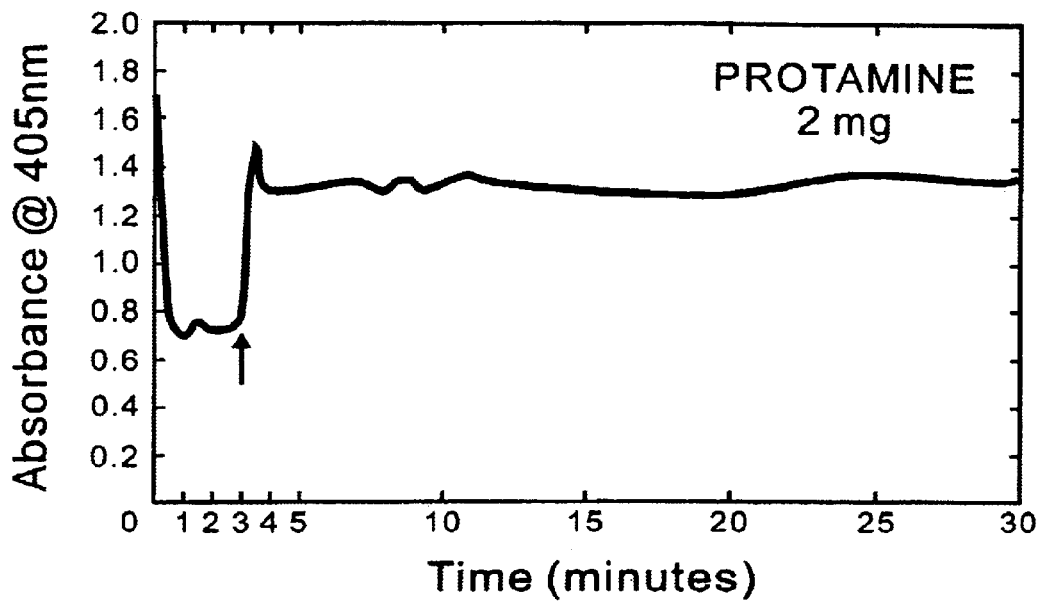
Figure 7F:
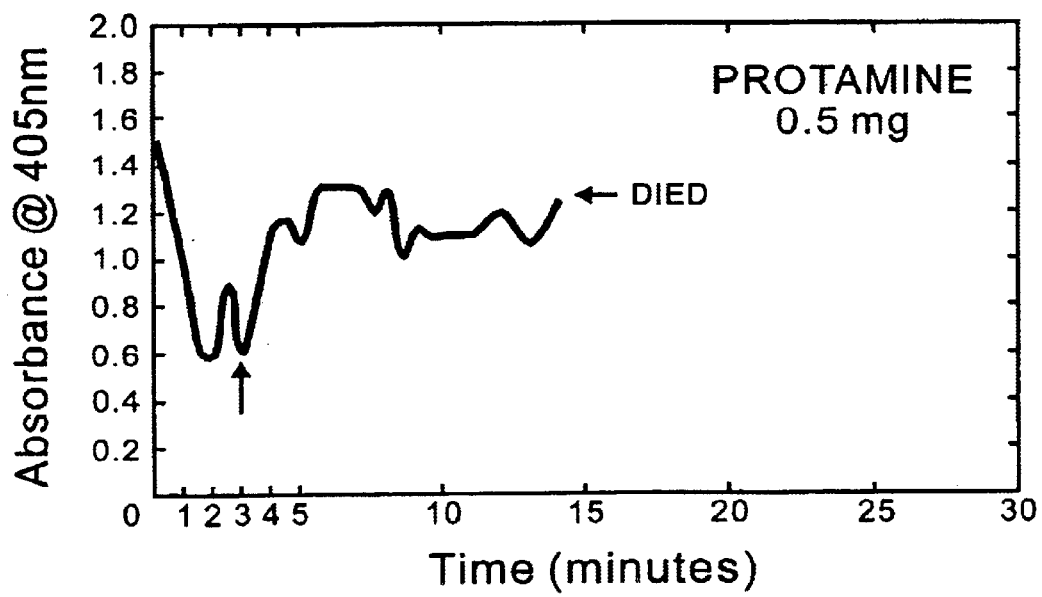
Figure 7G:
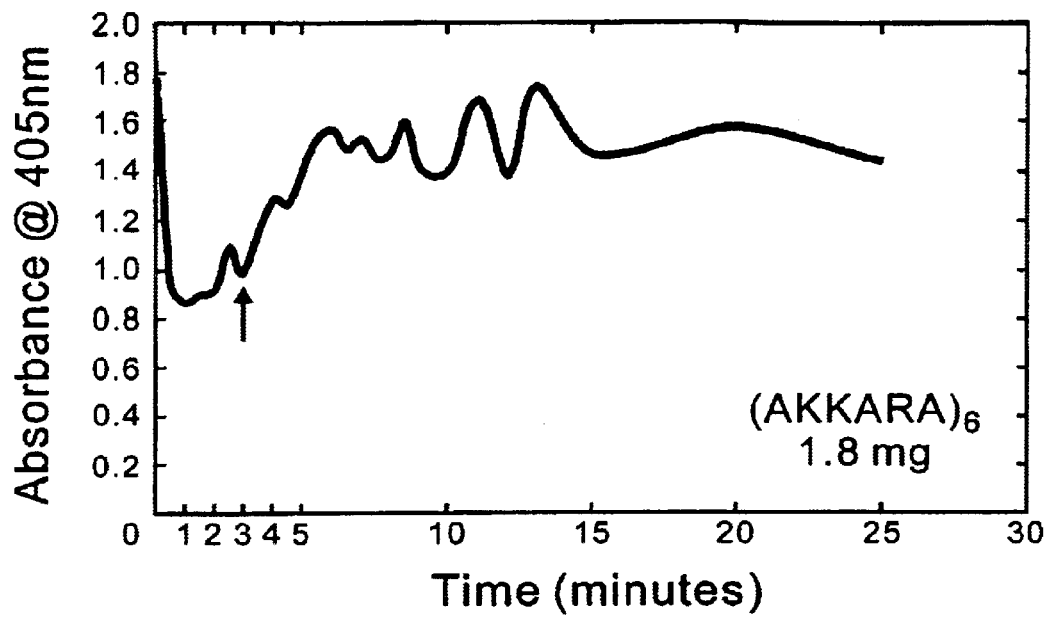
Figure 7H:
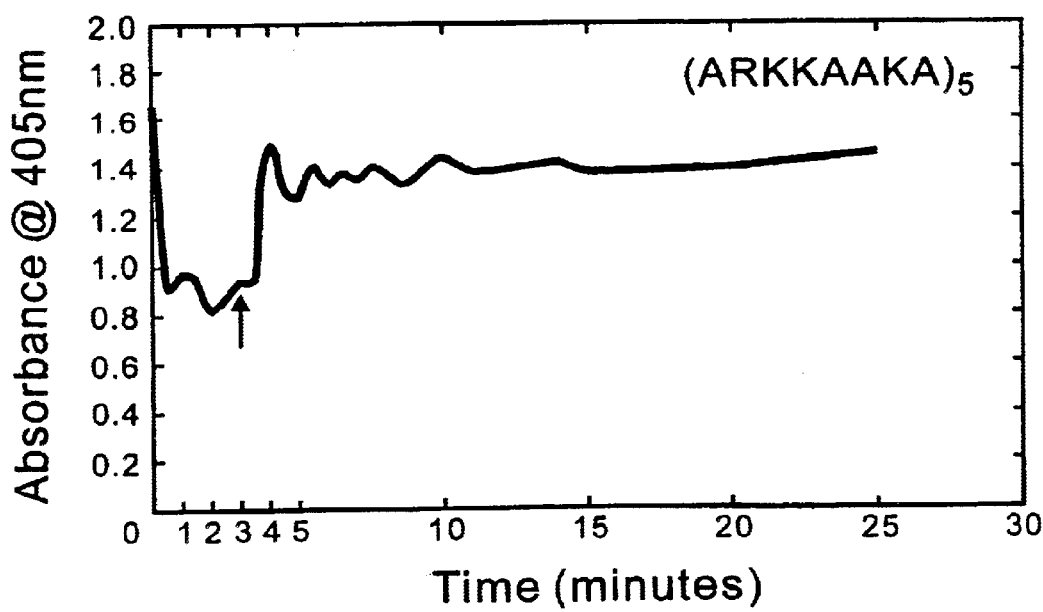
Figure 7I:
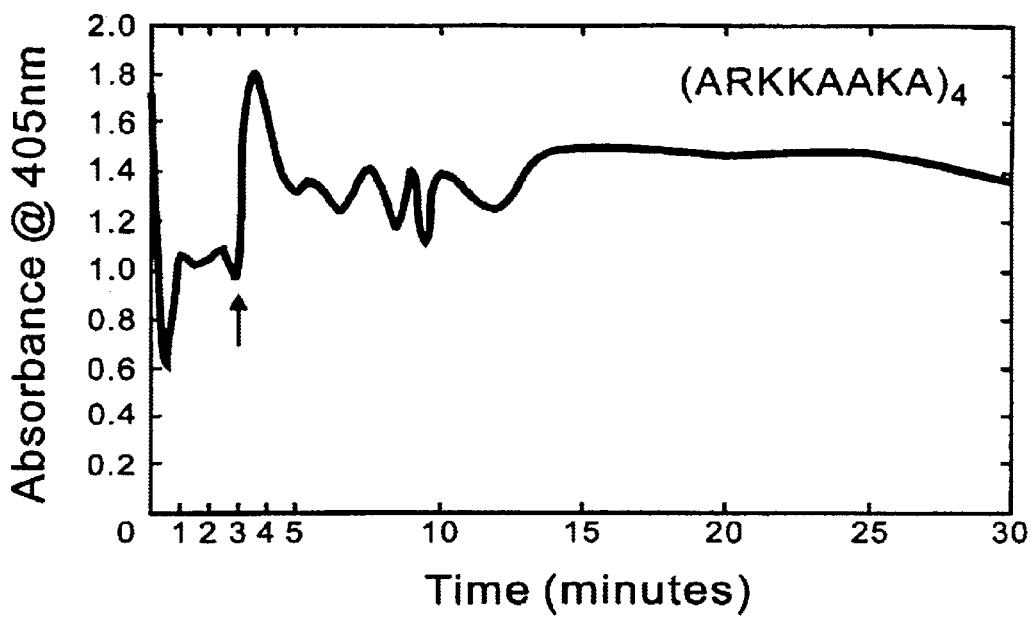
Figure 7J:
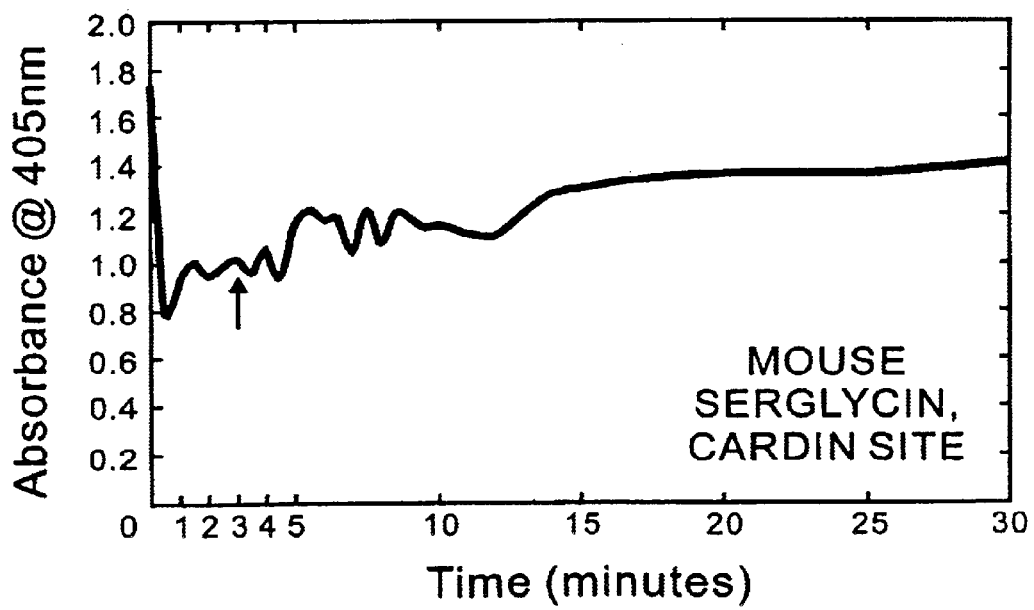

The maximal concentration of Lovenox in the plasma was 1.0 U/ml anti-Factor Xa activity for all the animals tested. The maximal plasma heparin concentration was found by 2–2.5 minutes after injection. About half the Lovenox was cleared from the circulation by 25–30 minutes after injection, in an approximately linear fashion for 15 minutes and more slowly thereafter. FIG. 7A shows a representative clearance curve. The three peptides at dosages shown in FIGS. 7B–D caused no removal of Lovenox above that due to direct clearance from the circulation alone (FIG. 7A). The peptide (ARKKPAKA)$_3$(FIG. 7D) appeared to delay clearance of the heparin from the circulation.

Protamine and three of our high affinity heparin-binding peptides [(AKKARA)$_6$, (ARKKAAKA)$_5$, and (ARKKAAKA)$_4$] neutralized the Lovenox concentration by at least 50%–80% within 2 minutes of injection of the peptide, the less tightly-binding mouse serglycin Cardin-site peptide was somewhat less effective, and there was no further clearance of Lovenox in all cases for the remainder of the 30-minute experiment (FIGS. 7E–J).

Summary:

A series of peptides have been generated, wherein said peptides have the ability to reverse the anti-FXa levels of Lovenox in rats within a few minutes at Lovenox concentrations to be expected in patients. The ability of these peptides to reverse the effects of Lovenox in vivo appears to be consistent with their ability to reverse the effects in vitro. The peptides reverse both anti-thrombin and anti-Xa activity of unfractionated heparin in vitro, and anti-Xa activity, unfractionated heparin, Lovenox, and Orgaran in vitro.

TABLE I

Heparin-binding affinity of peptides containing heparin-binding consensus sequences Peptides were analyzed for heparin-binding affinity by ACE, and $K_{ds}$ of peptide-heparin interactions were calculated from binding plots as detailed in Experimental Procedures. Each sample was tested for heparin-binding three to eleven times, with an average of four times. $K_d$ represents an average of data obtained for all trials ± standard deviation (S.D.); $^+$p values < 0.01 versus (AKKARA)$_4$ (SEQ. ID. NO:51) and $^{++}$p values < 0.01 versus (AKKARA)$_3$ (SEQ. ID. NO:7); *p values < 0.01 and **p values < 0.05 versus (ARKKAAKA)$_3$ (SEQ. ID. NO:43).

| Peptide Sequence | $M_r$ | $K_d$, (nM) ± S.D. |
|---|---|---|
| XBBXBX tandem repeats | | |
| AKKARA (SEQ. ID. NO:4) | 644 | Not detectable |
| (AKKARA)$_2$ (SEQ. ID. NO:14) | 1270 | 40,000 ± 18,000 |
| (AKKARA)$_3$ (SEQ. ID. NO:7) | 1895 | 1,900 ± 210$^+$ |
| (AKKARA)$_4$ (SEQ. ID. NO:51) | 2520 | 174 ± 19 |
| (AKKARA)$_5$ (SEQ. ID. NO:41) | 3146 | 94 ± 41$^+$ |
| (AKKARA)$_6$ (SEQ. ID. NO:13) | 3770 | 104 ± 32$^+$ |
| (ARRAKA)$_3$ (SEQ. ID. NO:54) | 1979 | 900 ± 170$^{++}$ |
| XBBBXXBX tandem repeats | | |
| ARKKAAKA (SEQ. ID. NO:5) | 843 | Not detectable |
| (ARKKAAKA)$_2$ (SEQ. ID. NO:6) | 1668 | 6,200 ± 3,000 |
| (ARKKAAKA)$_3$ (SEQ. ID. NO:43) | 2493 | 135 ± 54 |
| (ARKKAAKA)$_4$ (SEQ. ID. NO:8) | 3318 | 42 ± 15* |
| (ARKKAAKA)$_5$ (SEQ. ID. NO:42) | 4143 | 51 ± 11* |
| (ARRRAARA)$_3$ (SEQ. ID. NO:55) | 2745 | 72 ± 22** |
| (AKAAKKRA)$_3$ (SEQ. ID. NO:56) | 2493 | 132 ± 93 |
| XBBBXXBX tandem repeats with hydropathic position modifications | | |
| (AKRKKAAKA)$_3$ (SEQ. ID. NO:57) | 2878 | 75 ± 41 |
| (GRKKGGKG)$_3$ (SEQ. ID. NO:44) | 2325 | 200 ± 98* |

TABLE I-continued

Heparin-binding affinity of peptides containing heparin-binding consensus sequences Peptides were analyzed for heparin-binding affinity by ACE, and $K_{ds}$ of peptide-heparin interactions were calculated from binding plots as detailed in Experimental Procedures. Each sample was tested for heparin-binding three to eleven times, with an average of four times. $K_d$ represents an average of data obtained for all trials ± standard deviation (S.D.); $^+$p values < 0.01 versus (AKKARA)$_4$ (SEQ. ID. NO:51) and $^{++}$p values < 0.01 versus (AKKARA)$_3$ (SEQ. ID. NO:7); *p values < 0.01 and **p values < 0.05 versus (ARKKAAKA)$_3$ (SEQ. ID. NO:43).

| Peptide Sequence | $M_r$ | $K_d$, (nM) ± S.D. |
|---|---|---|
| (LRKKLGKR)$_3$ (SEQ. ID. NO:45) | 2959 | 105 ± 37 |
| (TRKKLGKI)$_3$ (SEQ. ID. NO:46) | 2794 | 737 ± 350* |
| (ARKKPAKA)$_3$ (SEQ. ID. NO:49) | 2571 | 360 ± 127* |
| ARKKAAKAARKKPAKAARKKAAKA (SEQ. ID. NO:50) | 2519 | 730 ± 340* |
| ARKKAAKARKKAKARKKAAKA (SEQ. ID. NO:58) | 2351 | 450 ± 95* |
| ARKKAAKAAAAAARKKAAKAAAAAARKKAAKA (SEQ. ID. NO:47) | 3062 | 254 ± 137* |

Native or modified serglycin sequences

| Peptide Sequence | $M_r$ | $K_d$, (nM) ± S.D. |
|---|---|---|
| YPARRARYQWVRCKP (SEQ. ID. NO:9) | 1948 | 187 ± 54 |
| YPTQRARYQWVRCNP (SEQ. ID. NO:10) | 1936 | 817 ± 170 |
| YPARRARYQWVRAKP (SEQ. ID. NO:12) | 1918 | 37,000 ± 6,700 |
| AAARRARAAAARAKA (SEQ. ID. NO:11) | 1482 | 72,000 ± 60,000 |

TABLE II

Percent Reversal of anti-Factor Xa Activity by Peptides in Vitro

Lovenox (Rhone Poulenc Rohrer), Orgaran (Organon), and unfractionated heparin (Sigma Chemical Co.) were added to plasma to obtain 0.5 U/ml anti-Factor Xa activity as determined by the Stachrom Heparin assay. The ATIII/heparin complex was allowed to form, the peptide was added at the indicated concentrations, and the residual Factor Xa activity was measured by a chromogenic assay according to the directions supplied with the kit. The percent reversal of heparin-like activity was determined. Each number represents the average of one-three duplicate or triplicate determinations, in which replicates were ±2%. Data were not obtained for areas left blank in the Table.

| Peptide | Type of Heparin | Peptide concentration in plasma | | |
|---|---|---|---|---|
| | | 0.6 mg/ml | 0.4 mg/ml | 0.12 mg/ml |
| (AKKARA)$_2$ (SEQ. ID. NO:14) | Lovenox | 61.5% | | |
| | Orgaran | 37.0% | | |
| | Heparin | 67.0% | | |
| (AKKARA)$_4$ (SEQ. ID. NO:51) | Lovenox | 73% | | |
| | Orgaran | 75% | | |
| | Heparin | 99% | | |
| (AKKARA)$_6$ (SEQ. ID. NO:13) | Lovenox | 82.5% | 86.5% | 86% |
| | Orgaran | 77% | 81.5% | 74.5% |
| | Heparin | 93% | 97.5% | 99% |
| (ARKKAAKA)$_4$ (SEQ. ID. NO:8) | Lovenox | 73% | | |
| | Orgaran | 70.5% | | |
| | Heparin | 87.5% | | |
| (ARKKAAKA)$_5$ (SEQ. ID. NO:42) | Lovenox | 81.5% | 71.0% | 68.5% |
| | Orgaran | 83.0% | 75.0% | 75.0% |
| | Heparin | 94.5% | 93.0% | 64.5% |
| (AKAAKKRA)$_3$ (SEQ. ID. NO:56) | Lovenox | 93.5% | | |
| | Orgaran | 72.0% | | |
| | Heparin | 94.0% | | |
| (ARKKPAKA)$_3$ (SEQ. ID. NO:49) | Lovenox | 100% | 62.5% | 62.0% |
| | Orgaran | 66.5% | 67.5% | 45.0% |
| | Heparin | 99.0% | 50.0% | 90.0% |
| (ARRRAARA)$_3$ (SEQ. ID. NO:55) | Lovenox | 67.5% | | |
| | Orgaran | 67.0% | | |
| | Heparin | 57.5% | | |

TABLE II-continued

Percent Reversal of anti-Factor Xa Activity by Peptides in Vitro
Lovenox (Rhone Poulenc Rohrer), Orgaran (Organon), and unfractionated heparin
(Sigma Chemical Co.) were added to plasma to obtain 0.5 U/ml anti-Factor Xa activity as
determined by the Stachrom Heparin assay. The ATIII/heparin complex was allowed to
form, the peptide was added at the indicated concentrations, and the residual
Factor Xa activity was measured by a chromogenic assay according to the directions
supplied with the kit. The percent reversal of heparin-like activity was determined.
Each number represents the average of one-three duplicate or triplicate determinations,
in which replicates were ±2%. Data were not obtained for areas left blank in the Table.

| Peptide | Type of Heparin | Peptide concentration in plasma | | |
|---|---|---|---|---|
| | | 0.6 mg/ml | 0.4 mg/ml | 0.12 mg/ml |
| ARKKAAKAARKKPAKAARKKAAKA (SEQ. ID. NO:50) | Lovenox | 83.0% | | |
| | Orgaran | 67.0% | | |
| | Heparin | 57.5% | | |
| YPARRARYQWVRCKP (SEQ. ID. NO:9) (murine serglycin) | Lovenox | 25.0% | | |
| | Orgaran | 16.5% | | |
| | Heparin | 77.0% | | |
| YPARRARYQWVRAKP (SEQ. ID. NO:12) (murine serglycin, cysteine replaced with alanine) | Lovenox | 0% | | |
| | Orgaran | 2.0% | | |
| | Heparin | 25.0% | | |
| YPTQRARYQWVRCNP (SEQ. ID. NO:10) (human serglycin) | Lovenox | 0% | | |
| | Orgaran | 5% | | |
| | Heparin | 90% | | |

TABLE III

Reversal of Anti-Thrombin Effects of Unfractionated Heparin by
Peptides in Vitro
Plasma was obtained from normal donors. Thrombin concentration
was standardized to produce a clotting time of 20–22 seconds.
Heparin was added at 0.5 U/ml. The clotting time for heparin alone
was approximately 3 minutes. One minute after addition of heparin
to the plasma, the peptides were added in concentrations ranging from
1–200 ug/ml. After one minute, thrombin was added and the clotting
time determined. The clotting time was normalized at
the peptide concentrations shown below.

| Peptide | μg peptide/ml heparinized plasma needed to normalize thrombin time |
|---|---|
| (AKKARA)$_6$ (SEQ. ID. NO:13) | 5 |
| (AKKARA)$_4$ (SEQ. ID. NO:51) | 10 |
| (AKKARA)$_2$ (SEQ. ID. NO:14) | >50 |
| (ARKKAAKA)$_5$ (SEQ. ID. NO:42) | 21 |
| (AKAAKKRA)$_3$ (SEQ. ID. NO:56) | >50 |
| YPTQRARYQWVRCNP (SEQ. ID. NO:10) (human serglycin) | 100 |
| YPARRARYQWVRCKP (SEQ. ID. NO:9) (mouse serglycin) | 15 |

We claim:

1. A synthetic peptide with a high affinity for glycosaminoglycans and proteoglycans of a formula selected from the group consisting of $(XBBBXXBX)_n$, $(XBXXBBBX)_n$, $(XBBXBX)_n$, and $(XBXBBX)_n$, wherein:
   each B is independently selected from the group consisting of arginine and lysine residues;
   each X is independently any amino acid residue; and
   n is at least 2.

2. A synthetic peptide according to claim 1, wherein n is from 2 to 6.

3. A synthetic peptide according to claim 2, wherein:
   each X is independently selected from the group consisting of alanine and glycine residues.

4. A synthetic peptide according to claim 3, wherein said peptide is selected from the group consisting of amino acid sequences SEQ ID NO:6, SEQ ID NO:7, SEQ ID NO:8, SEQ ID NO:13, SEQ ID NO:41, SEQ ID NO:42, SEQ ID NO:43, SEQ ID NO:44, SEQ ID NO:49, SEQ ID NO:51, SEQ ID NO:54, SEQ ID NO:55, SEQ ID NO:56.

5. A synthetic peptide according to claim 1, which comprises at least one D-amino acid residue.

6. A synthetic peptide according to claim 2, which comprises at least one D-amino acid residue.

7. A synthetic peptide of a formula selected from the group consisting of $(XBBBXXBX)_n$, $(XBXXBBBX)_n$, $(XBBXBX)_n$, and $(XBXBBX)_n$, wherein:
   each B is independently selected from the group consisting of arginine and lysine residues;
   each X is independently any amino acid residue;
   n is at least 2;
   provided that a single cysteine residue is contained in said synthetic peptide at an X position within three amino acid residues of the N-terminus or the C-terminus of said synthetic peptide.

8. A synthetic peptide according to claim 7, wherein n is from 2 to 6.

9. A synthetic peptide according to claim 8, wherein:
   each X is independently selected from the group consisting of cysteine, alanine and glycine residues.

10. A synthetic peptide according to claim 9, wherein said peptide is selected from the group consisting of amino acid sequences SEQ ID NO:35, SEQ ID NO:36, SEQ ID NO:37, and SEQ ID NO:38.

11. A synthetic peptide according to claim 7, which comprises at least one D-amino acid residue.

12. A synthetic peptide according to claim 8, which comprises at least one D-amino acid residue.

13. A synthetic concatameric peptide with a high affinity for glycosaminoglycans and proteoglycans wherein the sequence of amino acid residues of said peptide is represented by at least two segments selected from the group consisting of XBBBXXBX, XBXXBBBX, XBBXBX, and XBXBBX, wherein:

said peptide does not comprise only XBBBXXBX segments;

said peptide does not comprise only XBXXBBBX segments;

said peptide does not comprise only XBBXBX segments;

said peptide does not comprise only XBXBBX segments;

each segment is separated from an adjacent segment by at least one of any amino acid residue;

each B is independently selected from the group consisting of arginine and lysine residues; and each X is independently selected from the group consisting of cysteine, alanine and glycine residues, provided that a single cysteine residue is contained in said synthetic peptide at an X position within three amino acid residues of the N-terminus or the C-terminus of said synthetic peptide.

* * * * *